United States Patent
Lindkvist et al.

(10) Patent No.: US 12,165,536 B2
(45) Date of Patent: Dec. 10, 2024

(54) SIMULATION-BASED TRAINING AND ASSESSMENT SYSTEMS AND METHODS

(71) Applicant: MENTICE INC., Chicago, IL (US)

(72) Inventors: Johan Lennart Lindkvist, Skene (SE); Anthony Gerald Gallagher, Newtownabbey (IE)

(73) Assignee: MENTICE, INC., Chicago, IL (US)

( * ) Notice: Subject to any disclaimer, the term of this patent is extended or adjusted under 35 U.S.C. 154(b) by 886 days.

(21) Appl. No.: 16/403,465

(22) Filed: May 3, 2019

(65) Prior Publication Data

US 2019/0340956 A1 Nov. 7, 2019

Related U.S. Application Data

(60) Provisional application No. 62/667,500, filed on May 5, 2018.

(51) Int. Cl.
*G09B 23/30* (2006.01)
*A61B 17/22* (2006.01)
*G06Q 10/0639* (2023.01)

(52) U.S. Cl.
CPC .............. *G09B 23/30* (2013.01); *A61B 17/22* (2013.01); *G06Q 10/06393* (2013.01)

(58) Field of Classification Search
CPC ................................ G09B 23/30; A61B 17/22
(Continued)

(56) References Cited

U.S. PATENT DOCUMENTS 4,642,055 A * 2/1987 Saliterman ........... G09B 23/285
434/268
6,106,301 A 8/2000 Merril
(Continued)

FOREIGN PATENT DOCUMENTS

CN 105976652 9/2016
JP 2008064824 3/2008
(Continued)

OTHER PUBLICATIONS

Annaswamy, "Development and evaluation of an epidural injection simulator with force feedback for medical training," Feb. 1, 2001, pp. 97-102 [Retrieved from the internet: url:https://www.researchgate.net/profile/Thiru_Annaswamy/publication/12017748_Development_and_evaluation_of_an_epidural_injection_simulator_with_force_feedback_for_medical_traning/links/Oc9605164a270ae2a300000.pdf.
(Continued)

*Primary Examiner* — Jay Trent Liddle
*Assistant Examiner* — Alyssa N Brandley
(74) *Attorney, Agent, or Firm* — Bryan Cave Leighton Paisner LLP

(57) ABSTRACT

This disclosure relates to systems, methods and techniques for implementing metric-based simulation training and assessment of operators for performing various medical procedures. Operators are able to practice the medical procedures on medical simulators that provide simulations of real-world medical procedures. The simulations can be used to train operators to develop new skill sets for performing the medical procedures or to assist trained operators with maintaining their existing skill sets. The medical simulators can include a training and assessment module that defines the procedural phases and sub-steps of the medical procedures, monitors a set of performance metrics during the simulations, and detects when errors have occurred during the simulations. Performance evaluation information can be output based on operators' performances during the simulated medical procedures. The performance evaluation information can provide feedback and recommendations for improving and/or maintaining skill sets.

20 Claims, 9 Drawing Sheets

(58) Field of Classification Search
USPC .......................................................... 434/267
See application file for complete search history.

(56) References Cited

U.S. PATENT DOCUMENTS

| | | | | |
|---|---|---|---|---|
| 6,544,041 | B1* | 4/2003 | Damadian | G09B 23/285 |
| | | | | 600/416 |
| 8,707,963 | B2* | 4/2014 | Davis | A61F 2/30 |
| | | | | 128/898 |
| 2001/0016804 | A1* | 8/2001 | Cunningham | G09B 23/285 |
| | | | | 703/7 |
| 2002/0168618 | A1* | 11/2002 | Anderson | G16H 50/50 |
| | | | | 434/262 |
| 2005/0181342 | A1* | 8/2005 | Toly | G09B 23/30 |
| | | | | 434/262 |
| 2008/0020362 | A1* | 1/2008 | Cotin | G09B 23/285 |
| | | | | 434/267 |
| 2008/0160488 | A1* | 7/2008 | Younkes | G09B 7/04 |
| | | | | 434/219 |
| 2009/0123896 | A1 | 5/2009 | Hu et al. | |
| 2010/0167249 | A1* | 7/2010 | Ryan | G09B 23/285 |
| | | | | 434/267 |
| 2011/0236868 | A1* | 9/2011 | Bronstein | G09B 23/30 |
| | | | | 434/267 |
| 2012/0064497 | A1 | 3/2012 | Wu | |
| 2014/0220527 | A1 | 8/2014 | Li et al. | |
| 2014/0272866 | A1* | 9/2014 | Kim | G09B 23/28 |
| | | | | 434/262 |
| 2014/0349264 | A1* | 11/2014 | Shabat | G16Z 99/00 |
| | | | | 434/267 |
| 2015/0079565 | A1* | 3/2015 | Miller | G16H 50/50 |
| | | | | 434/262 |
| 2015/0100290 | A1* | 4/2015 | Falt | G16H 50/50 |
| | | | | 703/2 |
| 2016/0155364 | A1* | 6/2016 | Piron | G01R 33/58 |
| | | | | 434/270 |
| 2016/0203732 | A1 | 7/2016 | Wallace et al. | |
| 2016/0314710 | A1* | 10/2016 | Jarc | G09B 23/28 |
| 2017/0243522 | A1* | 8/2017 | Feins | G09B 23/285 |
| 2018/0116724 | A1 | 5/2018 | Gmeiner et al. | |
| 2019/0090969 | A1* | 3/2019 | Jarc | A61B 34/35 |

FOREIGN PATENT DOCUMENTS

| | | |
|---|---|---|
| JP | 2008070847 | 3/2008 |
| JP | 2015519596 | 7/2013 |
| JP | 2017510826 | 4/2017 |
| WO | 2015027286 A1 | 3/2015 |

OTHER PUBLICATIONS

Gallagher, "Metric-based simulation training to proficiency in medical education:—What it is and how to do it", Ulster Med J 2012; 81(3):107-113.

Patel, et al. "Learning Curves and Reliability Measures for Virtual Reality Simulation in the Performance Assessment of Carotid Angiography," Journal of the American College of Cardiology, vol. 47, No. 9, May 2, 2006 pp. 1796-1802.

Mitchell, et al. "A systematic review of assessment of skill acquisition and operative competency in vascular surgical training," Journal of Vascular Surgery, vol. 59, No. 5, Mar. 19, 2014 pp. 1440-1455.

Koehler et al., "The Arthroscopic Surgical Skill Evaluation Tool (ASSET)", Am. J. Sports Med., Jun. 2013; 41(6): 1229-1237.

Gallagher, et al. "Virtual Reality Simulation for the Operating Room Proficiency-Based Training as a Paradigm Shift in Surgical Skills Training," Annals of Surgery vol. 241, No. 2, Feb. 2005.

* cited by examiner

SIMULATION-BASED TRAINING AND ASSESSMENT SYSTEMS AND METHODS

CROSS-REFERENCE TO RELATED APPLICATIONS

This application claims priority to, and the benefit of, U.S. Provisional Patent Application No. 62/667,500 filed on May 5, 2018. The content of the aforementioned application is hereby incorporated by reference in its entirety.

TECHNICAL FIELD

This disclosure relates generally to medical simulators that are configured to utilize metric-based training techniques to assist medical practitioners with developing and/or maintaining skill sets associated with performing medical procedures.

BACKGROUND

A problem in the medical field relates to adequately training medical practitioners (e.g., doctors or medical students) to perform medical procedures, such as surgical procedures. Allowing inexperienced or lesser experienced medical practitioners to perform such procedures can be very dangerous to the patients being operated on. On the other hand, restricting medical practitioners from performing the procedures makes it difficult for the medical practitioners to develop the necessary skill sets for performing the procedures.

Traditionally, the skills required to practice medicine have been acquired in an apprenticeship fashion, such that new generations of medical practitioners acquired their skills "on-the-job" while assisting experienced medical practitioners with caring for patients. Although this traditional approach has been successful for learning certain types of skills, it has not been adequate for a variety of modern medical procedures. For example, the traditional apprenticeship approach has been shown to be inadequate with respect to teaching skills associated with image-guided interventional procedures (e.g., such as minimally invasive surgery (MIS)), endovascular catheter-based procedures, and the like.

Another related problem pertains to ensuring that trained medical practitioners maintain their skill sets over time. A medical practitioner's skill set for performing a specific surgical procedure, or other medical procedure, can diminish over time as a result of the medical practitioner performing a limited number of procedures. For example, a medical practitioner's psychomotor skills may diminish or extinguish over time if they are not used consistently. Problems relating to maintaining medical practitioners' skill sets can be particularly prevalent in areas that have smaller populations or in areas that have a relatively large number of medical practitioners in comparison to the number of procedures that are performed in the area. Both situations tend to result in smaller numbers of procedures being performed by many individual practitioners.

The current paradigms used for developing and/or maintaining skill sets of the medical practitioners are plagued with a variety of problems. They are too expensive (e.g., in terms of both time and money) and the results demonstrate that they are ineffective. This is due, at least in part, to the fact that the current paradigms do not provide a means for clearly, objectively and unambiguously assessing a medical practitioner's performance of a medical procedure. Instead, the operational aspects for the medical procedure are loosely defined in an abstract manner that makes it difficult to accurately assess the medical practitioner's performance. In many cases, the current paradigms also require inexperienced medical practitioners to train on real patients, which causes risks to the patients and increases costs for the health care providers.

The aforementioned problems associated with training medical practitioners and maintaining their skill sets applies to a wide variety of medical procedures including, but not limited to, endovascular surgical procedures. To demonstrate by way of example, consider the skill sets required to perform a mechanical thrombectomy procedure, which is commonly used to treat an acute ischemic stroke (AIS). During the procedure, a catheter is typically inserted into an artery located in the groin of a patient and threaded up to the patient's brain using X-ray guided imaging. When the catheter reaches a blood clot which caused the stroke, a stent retriever or other similar device is then inserted into the catheter to remove the blood clot and, in some cases, a stent device or balloon device is deployed into the artery.

The mechanical thrombectomy procedure is a difficult and complex procedure which should be performed safely, efficiently and according to best practices in order to provide the best possible patient outcomes. It is highly desirable that medical practitioners who perform these procedures do so continuously to ensure their skill sets are effectively maintained. In fact, some experts in the medical field have suggested that medical practitioners performing these operations should carry out 50 or more procedures per year in order to maintain their skill sets. However, as mentioned above, this may not be possible for many reasons, such as the small populations in certain geographic regions or the abundance of stroke centers or medical practitioners able to perform the procedures, both of which can decrease the total volume of procedures performed by individual medical practitioners.

In the United States, there is an abundance of stroke centers relative to the volume of AIS cases. In practice, this means that stroke centers performing higher volumes of mechanical thrombectomy procedures in Untied States are still falling short of performing the recommended threshold number of procedures for maintaining practitioner skill sets, while the stroke centers performing lower volumes of these procedures fall far below the recommended threshold. Consequently, medical practitioners in the United States are not performing the suggested volume of procedures to maintain their skill sets, which creates significant risks of reducing the quality of the procedures being performed. In fact, statistics show that, when the best and worst stroke center in any region is compared, the outcome of the procedures vary greatly with respect to experiencing complications (such that the complication rate can be approximately 3 to 4 times higher in the worst centers). Many experts believe that the morbidity and mortality rate of the patients is directly tied to the volume of procedures performed by the medical practitioners at the stroke centers.

In view of the foregoing, it is desirable to provide a training platform that enables lesser experienced medical practitioners to develop skills safely and effectively before performing real-world medical procedures on real patients, and which enables experienced medical practitioners to maintain or enhance their skills during time periods when they are not performing real-world medical procedures.

BRIEF DESCRIPTION OF DRAWINGS

The inventive principles are illustrated in the figures of the accompanying drawings which are meant to be exemplary and not limiting, in which like references are intended to refer to like or corresponding parts, and in which.

DETAILED DESCRIPTION OF EXEMPLARY EMBODIMENTS

Figure 1A:
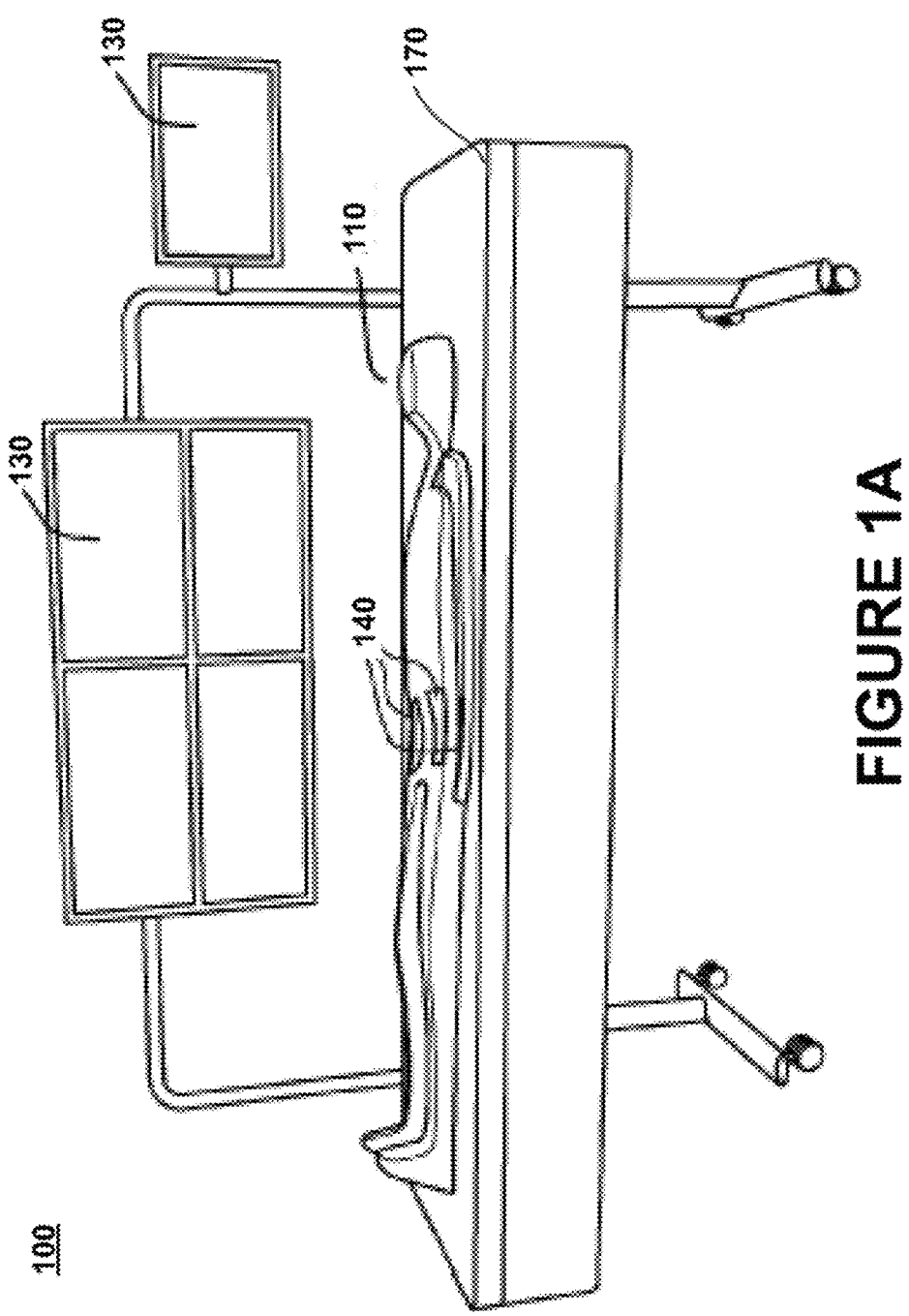
FIG. 1A is an exemplary medical simulator in accordance with certain embodiments.

This disclosure relates to novel systems, methods and techniques for implementing metric-based simulation training that facilitates the effective and efficient training and assessment of medical practitioners for performing various medical procedures. Medical practitioners are able to practice the medical procedures on medical simulators that provide simulations of real-world medical procedures. The simulations can be used to train medical practitioners to develop skill sets for performing the medical procedures and/or to assist trained medical practitioners with maintaining their skill sets. As explained in further detail below, the simulations described herein can be implemented using metric-based training techniques that provide the medical practitioners with varying exercises and training activities, and which compare metrics that are monitored during the simulations to pre-defined benchmarks in order to assess the performance of the medical practitioners. The exercises and training activities are provided using an iterative training model that assists the medical practitioners with reaching and/or maintaining a certain level of proficiency with respect to performing the medical procedures.

The configurations of the medical simulators providing the simulations can vary. In certain embodiments, the medical simulators can include tools for performing the medical procedures, simulation interface devices that include physical assemblies for receiving the tools during the simulations, and a feedback system (e.g., including one or more display devices and/or haptic feedback tools) for outputting information during the simulation. The medical practitioners engaging in the simulations may insert tools into the simulation interface devices and manipulate the tools inside of the simulators during the simulated medical procedures. The feedback system can provide information during the procedures to assist the medical practitioners with performing the procedures. For example, a display system can output a simulated x-ray imaging feed (e.g., or other imaging modality such as those mentioned below) that shows the tools being inserted and moved about a simulated anatomy in real-time during an endovascular procedure. The feedback system can also display assessment information that can assist the medical practitioners with developing and/or maintaining their skill sets (e.g., by outputting information that analyzes the performance of the medical practitioners during the simulations and/or providing recommendations for advancing the skill sets of the medical practitioners).

The tools used for medical simulators may generally include any type of medical tool or device that is used to perform a medical procedure, and can vary based on the type of medical procedure being simulated. For example, if a medical simulator is configured to simulate a mechanical thrombectomy procedure to treat a blood clot resulting from an acute ischemic stroke (AIS), the medical simulator may be equipped with guide wires, catheters, sheaths and balloon guides, aspiration devices, stent retrievers, stents and/or other tools. Such tools may be physical, specialized tools that are adapted for use with the simulations, actual tools used for real-life procedures, and/or combinations of the same. The medical simulators can be equipped with other types of tools for other types of medical procedure simulations. For example, the tools can include TEE probes and ICE catheters for diagnostics and echo-guided procedures, and IVUS/FFR/OCT catheters for intra-coronary diagnostics and guiding procedures.

The structures of the simulation interface devices can vary. For example, as illustrated in FIGS. 1A-1D (described below), the simulation interface devices may include full body mannequins that simulate patients, devices that have human-shaped figures integrated into upper surfaces of the simulation interface devices, and/or portable, box-shaped simulation interface devices. Other configurations can also be used for the simulation interface devices. Endovascular simulators, for example, may include simulation interface devices that comprise one or more openings that enable insertion of the tools during the simulations of the medical procedures. The simulation interface devices (or other system component of the medical simulators) may include software that is configured to generate simulations of a human anatomy (e.g., in some cases, as shown via a simulated x-ray imaging display or other imaging modality). As tools are inserted into simulators via the openings in the simulation interface devices, sensors incorporated into the simulation interface devices sense the tools and track the movement of the tools inside of the simulators. The movement of the tools is displayed in the simulations that are output by the feedback system. For example, in the context of a simulation for a mechanical thrombectomy procedure, the simulations may display the movement of catheters, stent retrievers and/or other devices being threaded through an artery as the tools are being inserted and moved inside of the simulator. In certain embodiments, haptic and/or tactile feedback may be provided to operators during the simulations through the tools. For example, the tools may vibrate or provide other touch sensitive feedback to the operators in response to the medical simulators detecting improper usage of the tools (e.g., scraping anatomic components, excessive force, usage of wrong tools, etc.). Similarly, the feedback can include forces computed by the simulation as a result of the interaction between devices or tools and the patient tissues, particularly the cerebral arteries.

The feedback systems can include devices for outputting any information related to the simulations. The feedback systems can include monitors, display devices, touch-screen devices, audio-output devices, and/or other hardware and software outputs. Certain feedback systems can display information about the simulation while the simulation is being conducted. In certain embodiments, the feedback systems output imaging simulations that provide video or images of a simulated human and associated anatomy as a simulation is being conducted. The imaging simulations output by the feedback system can be based on any type of imaging modality including, but not limited to, x-ray modalities, ultrasound modalities, magnetic resonance imaging (MRI) modalities, computed tomography (CT) imaging modalities, 3-D mapping modalities, or any combination thereof. For example, as the medical practitioner inserts the tools into the simulation interface device during the simulation, a display device may display a simulated real-time imaging or video feed that provides a simulation of the tool being inserted into an actual human's body (e.g., which illustrates the tool being inserted and retracted from a human body). In certain embodiments, these feedback systems may also be used to configure settings for the simulations and medical simulators, and to provide feedback after the simulations have been conducted (e.g., to display the results of assessing the medical practitioners' performance and provide recommendations to the medical practitioners aimed at improving their skills).

The medical simulators are configured to execute a training and assessment module that characterizes the medical procedures being simulated, monitors and assesses the performance of the medical practitioners performing the medical procedure using the medical simulator, and assists the medical practitioners with developing and/or maintaining their skill sets. The training and assessment module can be configured to, inter alia, define the procedural phases and sub-steps of the medical procedures, define a set of metrics to be tracked and monitored during the simulations, determine if and when the phases and sub-steps of the medical procedures are completed during the simulation and actively guide the medical practitioners through the steps and phases, detect when errors have occurred during the simulations based on specified error criteria, compare the performance (e.g., including the monitored metrics) of medical practitioners to pre-defined benchmarks, provide recommendations (e.g., such as recommended simulation exercises to enhance skills in certain areas) to assist the medical practitioners with advancing and/or maintaining their skill sets, and/or facilitate advancement of the medical practitioners' skill levels (e.g., novice, competent, expert, etc.).

An important function of a simulation is to facilitate the effective and efficient training of skill sets outside the clinical setting, thus minimizing risks to the patients due to learning curves of novice medical practitioners. To accomplish this, the training and assessment module stores data that is based on a detailed task analysis of a medical procedure (or a plurality of medical procedures) that enables the simulations to achieve this goal. Units of performance that have been identified and validated as being integral or significant to the skilled performance of a medical procedure are captured as metrics for the procedure. These validated metrics can be used to define and shape the configuration of any type of simulation which is developed to train a medical practitioner to skillfully execute the tasks which are performed in connection with a medical procedure. The metrics are unambiguously and objectively defined by the training and assessment module so that they can be monitored and scored during the simulation. The metrics enable the training and assessment module to capture the essence of a real-world performance, and to compare a medical practitioner's performance during a simulation against objective data that can be used to assess the medical practitioner's performance during a simulation.

The simulations can be configured to execute in a training mode or a test mode. The training and assessment module includes all of the programming logic, settings and data associated with implementing the training and test modes. When the simulations are in training mode, the metrics are used to provide live, proximal feedback and guidance throughout the procedure. For example, the medical practitioners will be notified of any errors committed during the simulations (e.g., via a warning messages, alert messages and/or error messages), and the feedback systems will actively guide the medical practitioners throughout the procedures (e.g., by telling them what the next steps are, and how they should be performed). During the training mode, the training and assessment module acts as a proctor in providing such assistance. In test mode, the training assistance is turned off. The warnings, alerts and guidance are not available in the simulations during test mode.

In certain embodiments, the metrics can be used to define, inter alia, the order in which the procedure steps or tasks are performed, the instruments to be used during each step and task, and an expected manner of using the instruments during the procedure. For each procedure step, the metrics may also describe what should not be done (e.g., by characterizing performance that deviates from optimal, sufficient or acceptable performance levels) and to identify errors. Capturing metric errors is important because it allows medical practitioners to target problematic procedure tasks or aspects that require improvement or attention, thus enabling the practitioners to eliminate, or at least reduce, the occurrence of errors during the medical procedures. Once again, this means that operational definitions of performance error metrics should be unambiguously and objectively defined to enable detection of the errors during the simulations. By precisely defining the metrics, the medical simulators are able to reliably compute scores for each of the metrics during the simulations based on the medical practitioner's performance across a variety of functions for skills training, and also across a variety of different experience levels.

The metrics derived from a detailed characterization of a medical procedure inform the training and assessment module to provide a simulation which offers an artificially created or configured "learning scenario" that allows medical practitioners to practice or rehearse all of the salient aspects of a procedure. The training and assessment module is configured to provide a wide span of appropriate sensory responses to the medical practitioner's physical actions that are behaviorally consistent with what would be experienced in a real-life procedure (e.g., including the ability to detect and respond to both appropriate actions engaged in during the simulations and inappropriate actions, such as errors, that are engaged in during the simulations). The simulations also afford the medical practitioner the opportunity to: i) perform the procedure, ii) based on the same ordering of tasks as would occur in real life situations, and iii) with the same devices that the procedure would normally be used with the procedure. As mentioned above, the training and assessment module is configured to provide the medical practitioners with reliable and valid metric-based assessment of their performance. The assessments made by the training and assessment module can be provided in a summative or collective fashion (e.g., by providing an overall summary of the medical performance as to certain tasks, metrics or aspects of the simulation) and/or in a formative or granular fashion with respect to the execution of each task associated with the medical procedure.

The metrification of the training and assessment module extends the learning techniques far beyond a basic educational experience to a more systematic training package. Based on current published evidence, this capacity has been shown to enhance skill development by 40-69%. These improvements allow for the measurement of "skill" as derived (and validated) from experienced practitioners, clinical guidelines and published evidence. For example, choosing the correct catheter or wire, the amount of fluoroscopy used, or time taken to perform the procedure are all different types of process measures. In addition to monitoring these types of metrics, the techniques described herein also allow for measuring of the quality (e.g., safety) of the medical practitioner's performance.

The settings of the training and assessment module can be configured to the specific medical procedure that is the subject of the simulation. For example, settings may include rules, parameters and programming logic for defining the procedural phases of the medical procedures, defining sub-steps for the phases, defining the metrics to be tracked and monitored during each of the steps and phases, and establishing benchmarks that can be used to determine whether a medical practitioner's performance during the simulation (e.g., based on the monitored metrics) was satisfactory. The training and assessment module can be configured differently for each specific medical procedure to account for the varying steps/phrases, metrics and benchmarks that are applicable to each medical procedure. The principles described herein can be adapted to implement a metric-based simulation training medical procedure for any type of medical procedure based on the principles described herein.

The discussion provided further below demonstrates exemplary phases, sub-steps, metrics and benchmarks that can be used to configure a training and assessment module for a simulation of a mechanical thrombectomy procedure. However, it should be recognized that the phases, sub-steps, metrics and benchmarks of the training and assessment module can vary based on the types of medical procedures.

There are numerous medical procedures in which metric-based learning techniques can be applied, and these techniques can be extended well outside the endovascular space. Any medical procedure in which the steps or tasks are measureable in a well-defined way may represent good candidates. For example, in the endovascular space, the metric-based learning techniques can be used to measure, inter alia, catheter and wire movements, stent and/or graft deployment and final positioning, artificial valve deployment and positioning, CRM lead or device positioning, electrophysiology measurements and ablation, imaging and measurement technologies such as fractional flow reserve (FFR)) and optical coherence tomography (OCT), and various ultrasound technologies such as transesophageal echocardiography (TEE), intracardiac echocardiography (ICE), and Intravascular ultrasound (IVUS).

In certain embodiments, the metrics that are monitored by the training and assessment module during a simulation include metrics that can be generally categorized into the following categories: (1) protocol adherence metrics; (2) safety metrics; (3) efficiency metrics; and (4) precision metrics. Each of these are described in further detail below.

The protocol adherence metrics can be used, inter alia, to monitor and determine whether the simulated procedure was performed according to best practices that have been defined in the stored criteria of the training and assessment module. Exemplary protocol adherence metrics may include metrics that determine whether each of the phases and associated sub-steps were completed during a simulation, whether the phases and sub-steps were completed in the appropriate order, whether the appropriate tools were used at the appropriate times during the simulation, and other types of related metrics. Each of the protocol adherence metrics computed during the simulation can be compared to a benchmark to determine whether or not the medical practitioner's performance during a simulation was acceptable or unacceptable with respect to a particular aspect of the medical procedure.

The safety metrics can be used, inter alia, to monitor and determine whether the simulated procedure was performed in a manner that would cause risk to a patient and/or whether errors were committed during the simulated procedure. Exemplary safety metrics can indicate whether certain anatomic components (e.g., blood vessels, organs, tissues, etc.) were inadvertently scraped or damaged during the simulation, whether a tool used during the simulation was out of view (e.g., not viewable on the feedback system because the tools were extended too far without adjusting the simulated imaging device), whether tools were pushed too far or excessive pressure was applied after resistance increased, whether tools were deployed in the wrong regions, and/or other similar types of errors. Each of the safety metrics computed during the simulation can be compared to a benchmark to determine whether or not the medical practitioner's performance during a simulation was acceptable or unacceptable with respect to a particular aspect of the medical procedure. In certain embodiments, haptic and/or tactile feedback may be provided to operators through the tools in response to determining that one or more monitored safety metrics (or other metrics) were not satisfied during a simulation.

The efficiency metrics can be used, inter alia, to monitor and determine whether the simulated procedure was performed in an efficient or skillful manner. Many of the metrics in this category may comprise cumulative or aggregated metrics that are based on an overall performance during the simulation, or an overall performance during a phase or sub-step of the simulation. Exemplary efficiency metrics may indicate whether the simulated procedure was completed in a timely fashion (e.g., the total procedure was completed in a timely fashion, or the individual phase of a procedure was completed in a timely fashion), whether the medical practitioner's use of the tools during the procedure was smooth (e.g., whether the tools were used in a manner that exhibited economy of movement during the simulated procedure with respect to the translational and/or rotational movement of the tools), whether the medical practitioner efficiently and/or effectively used the imaging equipment (e.g., reflecting the total time the medical practitioner used fluoroscopy and/or the total syringe volume used for contrast) during the simulated procedure, and/or other similar types of metrics. Many of the efficiency metrics have a direct impact on the safety of the simulated patient (e.g., excessive procedure times result in higher risk for complications, excessive anesthesia times increase patient risks, excessive radiation exposure increase patient risks, etc.). Each of the efficiency metrics computed during the simulation can be compared to a benchmark to determine whether or not the medical practitioner's performance during a simulation was acceptable or unacceptable with respect to a particular aspect of the medical procedure.

The precision metrics can be used, inter alia, to monitor and determine whether the simulated procedure, or tasks associated with the simulated procedure, was performed with proper precision. Exemplary precision metrics may indicate whether a correctly sized tool (e.g., stent) was place at or near an optimal position, whether a medical practitioner ablated material precisely along a predefined path, and/or whether fluids were injected exactly or close to required amounts (e.g., whether precise amounts of embolization liquids were inject into an arteriovenous malformation). Like the safety metrics, many of the precision metrics have a direct impact on the safety of the simulated patient. Each of the precision metrics computed during the simulation can be compared to a benchmark to determine whether or not the medical practitioner's performance during a simulation was acceptable or unacceptable with respect to a particular aspect of the medical procedure.

While certain portions of this disclosure may characterize metrics as being associated with a particular category (e.g., protocol adherence, safety, efficiency, and precision), it should be recognized that many metrics described herein can be associated with, or included in, multiple categories.

As mentioned above, each of the metrics computed by the training and assessment module can be compared to a benchmark. The benchmark can represent a value that is used to determine whether the medical practitioner satisfied a particular requirement or aspect of the medical procedure. In certain embodiments, the benchmarks may be established during a calibration phase of the training and assessment module in which experienced medical practitioners or experts perform the simulated medical procedures to set parameters that reflect proficiency in performing the medical procedures. During the calibration phase, the performance metrics of the experienced medical practitioners or experts are tracked and used to establish appropriate benchmarks for the medical procedures. In some cases, the benchmarks may be updated based on the results of simulations performed by the medical practitioners over time. In other embodiments, the benchmarks can be based on expected values or theoretical values for various aspects of the medical procedures and the values can be specified or entered by a user via an input device.

In certain embodiments, each benchmark and/or metric is associated with a logical operator (e.g., a setting associated with a Boolean operator or symbol) that is used to compare the metric computed during the simulation with the pre-defined benchmark to determine if the benchmark is satisfied. For example, a "total time" metric may be associated with a benchmark that indicates a period of time (e.g., 1,369 seconds) in which a procedure should be completed. In this example, the benchmark and metric may be associated with a logical operator that indicates that the metric value should be less than or equal to the benchmark value (e.g., metric<=benchmark).

Any type of logical operator may be associated with a metric/benchmark pair including the following logical operators: equals (=); less than (<); greater than (>); less than or equal to (<=); greater than or equal to (>=); not equal (!=); etc. Thus, after a simulated procedure is performed, each of the monitored metrics may be compared to an associated benchmark using the logical operator assigned to the metric/benchmark pair. If the result of this comparison is TRUE, then the training and assessment module determines that the individual satisfied an aspect or requirement of the procedure (e.g., determines that the procedure was performed in a timely manner). On the other hand, if the result of this comparison is FALSE, then the training and assessment module determines that the individual did not satisfy that aspect or requirement of the procedure.

After a simulation is performed, the training and assessment module can generate a detailed report that summarizes information associated with the procedure. The detailed report can provide a detailed listing of the metrics that were monitored during the procedure, the pre-defined benchmarks associated with each of the metrics, and proficiency indicators that identify whether or not the medical practitioner satisfied benchmarks. The detailed report can be presented via the feedback system and/or in other suitable ways.

The training and assessment module can also be configured to analyze the results that make up a detailed report, or a collection of detailed reports (e.g., relating to multiple simulated procedures performed by a medical practitioner), in order to provide recommendations to the medical practitioners and/or to present medical practitioners with related information. For example, the recommendations and/or information presented can be used to identify skills that could use improvement, to identify skills in which the medical practitioner has shown proficiency, to recommend simulated exercises to assist the medical practitioner with developing and/or maintaining certain skills, and provide other types of related feedback. The recommendations output by the training and assessment module can be used in an iterative manner to enhance the skills of the medical practitioners.

As evidenced by the disclosure herein, the inventive principles set forth in this disclosure are rooted in computer technologies that overcome existing problems with training medical practitioners and maintaining skill sets of medical practitioners. The principles also are rooted in computer technologies that provide simulations of medical procedures that monitor, track, display and update simulation information in real-time as the medical procedure is being conducted (e.g., by displaying real-time x-ray imaging simulations which demonstrate how surgical tools are being inserted and removed from a physical simulator). The training and assessment module is configured with a ruleset that clearly and objectively defines the metrics, phases, error criteria and/or other related information for the medical procedures. This ruleset is used in conjunction with the real-time monitoring of the medical practitioners' actions to assess the performance of the medical practitioners during the simulations. This technology-based solution marks an improvement over existing computing capabilities and functionalities related to simulating medical procedures and assessing medical practitioner performance, at least in part, by implementing a metric-based monitoring solution that can be used to objectively assess performance and to recommend simulated exercises for improving or maintaining skill sets. These techniques are designed to improve the way medical practitioners are evaluated, to assist the medical practitioners with developing and/or maintaining their skill sets, and, as a result, improve healthcare outcomes for patients undergoing medical procedures.

The medical simulators and/or each of their components (e.g., the simulation interface devices, tools and feedback system) may include one or more processor devices (e.g., central processing units or CPUs) that are in communication with one or more computer storage devices (e.g., RAM, ROM, PROM, SRAM, etc.). The computer storage devices are preferably physical, non-transitory mediums. The storage medium can store applications, software code, databases and other data that is related to performing any of the functions described in this disclosure pertaining to the medical simulators, the simulations (e.g., x-ray guided simulations of a human anatomy) and/or the training and assessment module utilized by the medical simulators. The one or more processor devices and one or more computer storage devices can be configured to execute the instructions stored on memory devices can be configured to perform such functions. The training and assessment module can be stored on and/or executed by the simulation interface devices or other components of the medical simulators.

As used herein the term "medical practitioner" is intended to be used in a very broad sense. For example, the term "medical practitioner" can be used to refer to a doctor, physician, medical student (e.g., pre-graduate or post-graduate student), nurse, healthcare professional, technician, and/or any other individual that utilizes or operates the medical simulator.

The embodiments described in this disclosure can be combined in various ways. Any aspect or feature that is described for one embodiment can be incorporated into any other embodiment mentioned in this disclosure. Moreover, any of the embodiments described herein may be hardware-based, software-based and, preferably, comprise a mixture of both hardware and software elements. Thus, while the description herein may describe certain embodiments, features or components as being implemented in software or hardware, it should be recognized that any embodiment, feature or component that is described in the present application may be implemented in hardware and/or software.

Some of the figures below demonstrate how the inventive principles discussed in this disclosure can be utilized to provide metric-based simulations for performing a mechanical thrombectomy procedure for ischemic strokes. However, the inventive principles are not limited to such and, instead, can be used to provide simulations for other types of medical procedures. One of ordinary skill in the art would recognize that the details provided below (e.g., with respect to the particular phases and sub-steps of the procedure, the metrics being monitored, the benchmarks that are established, etc.) can be varied and adapted to accommodate other types of medical procedures.

FIGS. 1A-1D illustrate exemplary medical simulators 100 that can be utilized in accordance with certain embodiments of the present principles. These simulators 100 illustrate examples of simulators 100 that can be used for endovascular procedures (e.g., such as a mechanical thrombectomy procedure). While the configurations and structures of the simulators used for other types of medical procedures can differ greatly in comparison to the exemplary simulators 100 shown in FIGS. 1A-1D, it should be recognized that the inventive principles described in this disclosure equally apply to these other types of simulators not shown in the figures.

Each medical simulator 100 includes a simulation interface device 110, one or more tools 120 (visible in FIG. 1B), and a feedback system 130. The simulation interface devices 110 in these figures include openings 140 for receiving the one or more tools 120. The tools can include catheters, stent retrievers, coil retrievers, aspiration devices, and/or other tools that may be used when performing a mechanical thrombectomy procedure. The tools can represent the actual physical tools that are used to perform real-world mechanical thrombectomy procedures, or can be specialized tools that are adapted for use with the simulation interface device. The feedback system 130 displays information associated with the simulations being conducted. For example, the feedback system 130 may display an x-ray image simulation that shows the tools 120 within a simulated human anatomy as the tools 120 are inserted into simulation interface device 110 via the openings 140. Similar to a real-world mechanical thrombectomy procedure, the medical practitioners engaging in the simulations can utilize the images provided by the feedback system 130 to perform the medical procedure. For example, simulated x-ray guided images can be used to guide the tools 120 into an artery located in the groin of a patient (e.g., via opening 140), to guide the tool up the artery to the patient's brain, to utilize the tools to remove a simulated blood clot, to deploy a device (e.g., a stent or balloon) into the artery near the location of the blood clot, and/or to retract the tools 120 from the simulation interface device 110. Once a simulation is completed, the feedback system 130 can display information related to the performance of the medical practitioner during the simulation (e.g., to highlight errors that were made and/or to show whether the monitored metrics met the pre-defined benchmarks).

Figure 1B:
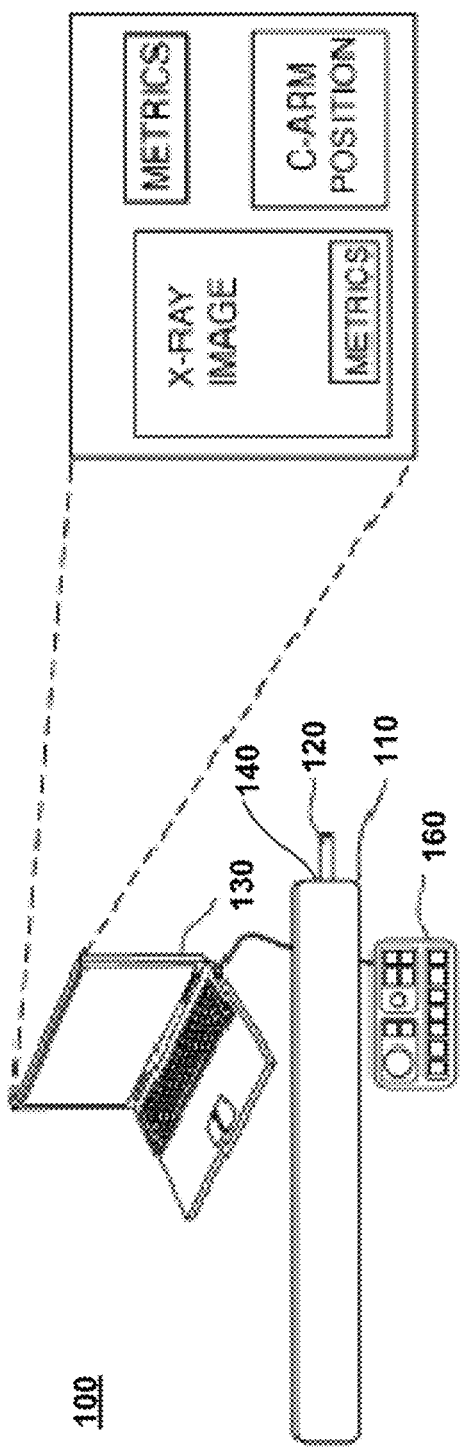
FIG. 1B is another exemplary medical simulator in accordance with certain embodiments.

The configurations of the medical simulators in FIGS. 1A-1D vary in different respects. For example, these figures demonstrate that the simulation interface device 110 can include full body mannequins that are physically similar to patients' bodies (FIGS. 1C-1D), human-shaped figures that are integrated into a surface 170 of the medical simulators (FIG. 1A), and/or portable, box-shaped simulation interface devices (FIG. 1B). Certain medical simulators 100 also may include x-ray machine 150 (FIG. 1D), such as mobile or stationary C-arm machine used in performing fluoroscopic-guided procedures, that can be used by the medical practitioners during the simulations to adjust the x-ray images that are displayed via the feedback system 130. For example, the simulated x-ray image displayed on the feedback system 130 may represent x-ray images that would have been generated by the x-ray machine at that position during a real procedure. Other types of simulated imaging modalities (e.g., ultrasound, MRI, CT imaging, 3-D mapping, etc.) can also be used with the medical simulators.

Figure 1C:
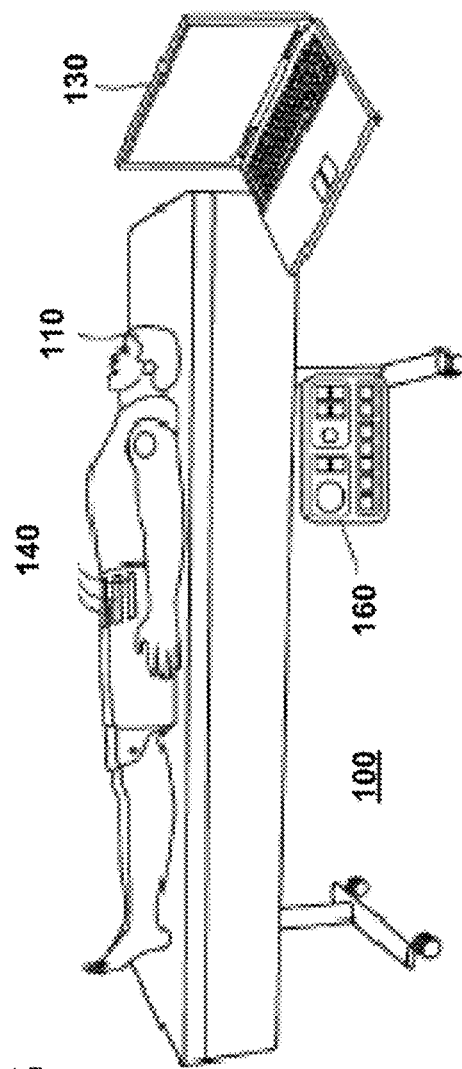
FIG. 1C is another exemplary medical simulator in accordance with certain embodiments.
Figure 1D:
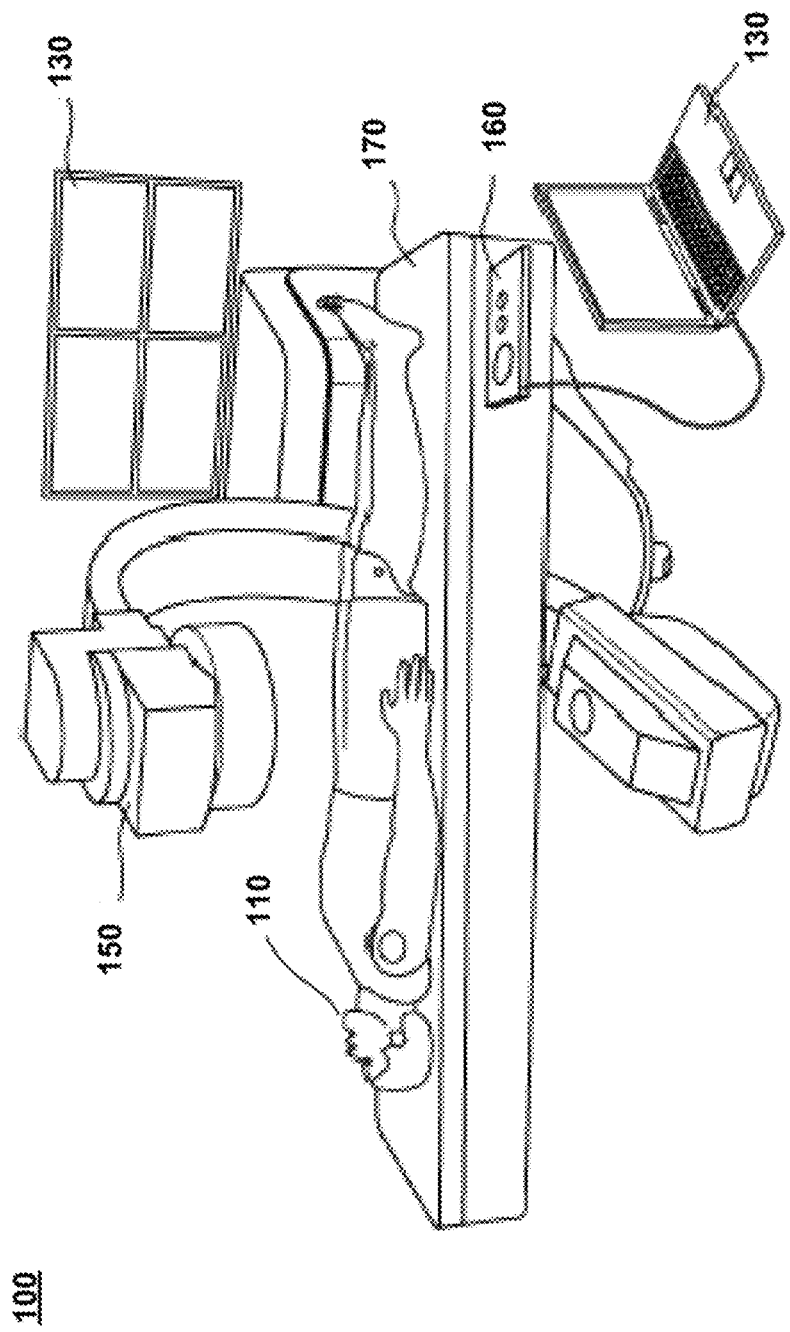
FIG. 1D is another exemplary medical simulator in accordance with certain embodiments.

The configuration of the feedback system 130 can also vary, e.g., such that it may include one or more touch screen displays (FIGS. 1A and 1D) and/or one or more computing devices (FIGS. 1B and 1C). Some of the medical simulators 110 also can include input devices 160 (FIGS. 1B, 1C and 1D) for adjusting the settings of the simulations, the settings of the simulated x-ray equipment 150 (or other imaging modalities), the settings of the feedback system 130, and/or other settings.

Figure 2A:
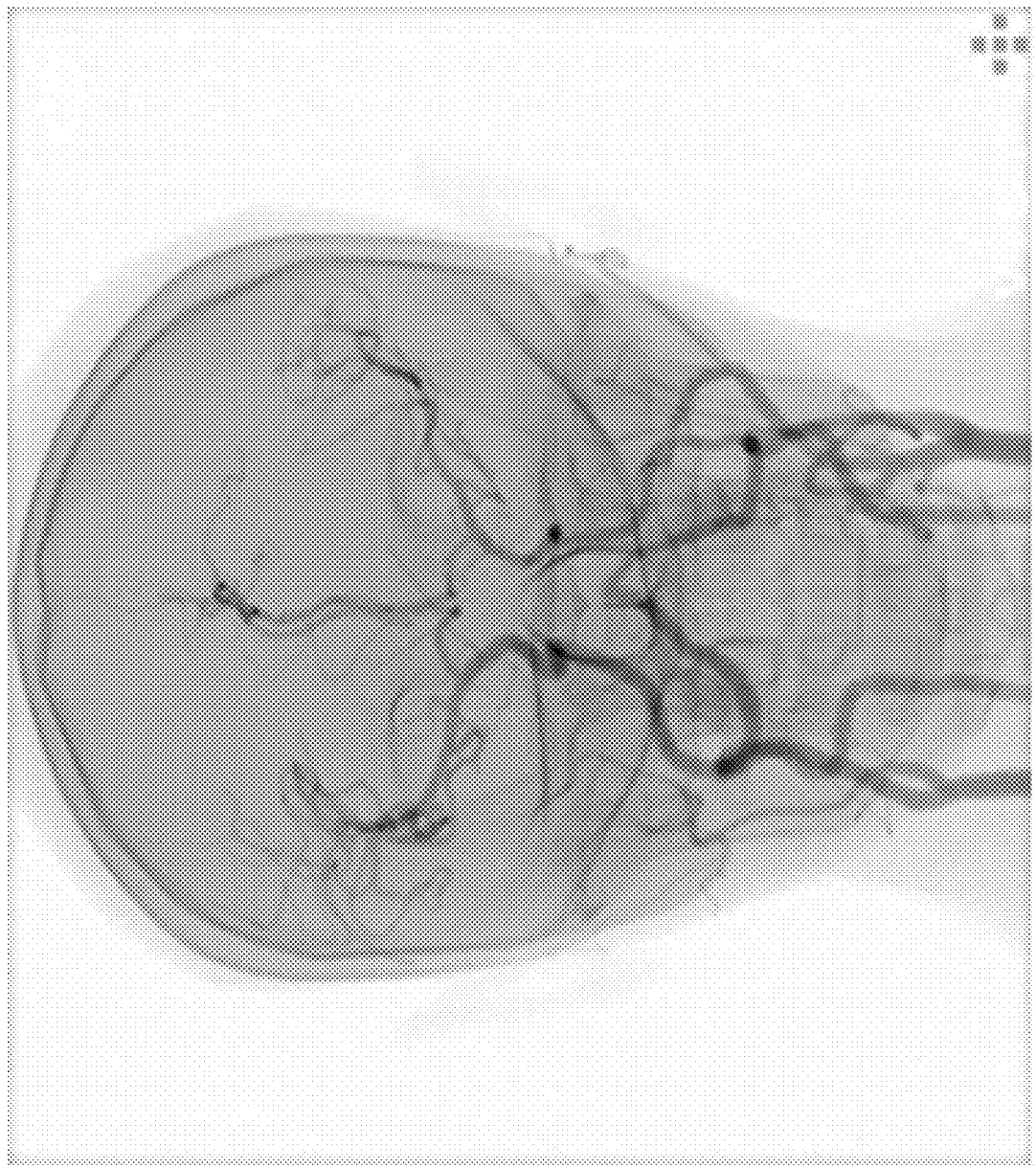
FIG. 2A is an exemplary x-ray image simulation that can be displayed by a feedback system in accordance with certain embodiments.
Figure 2B:
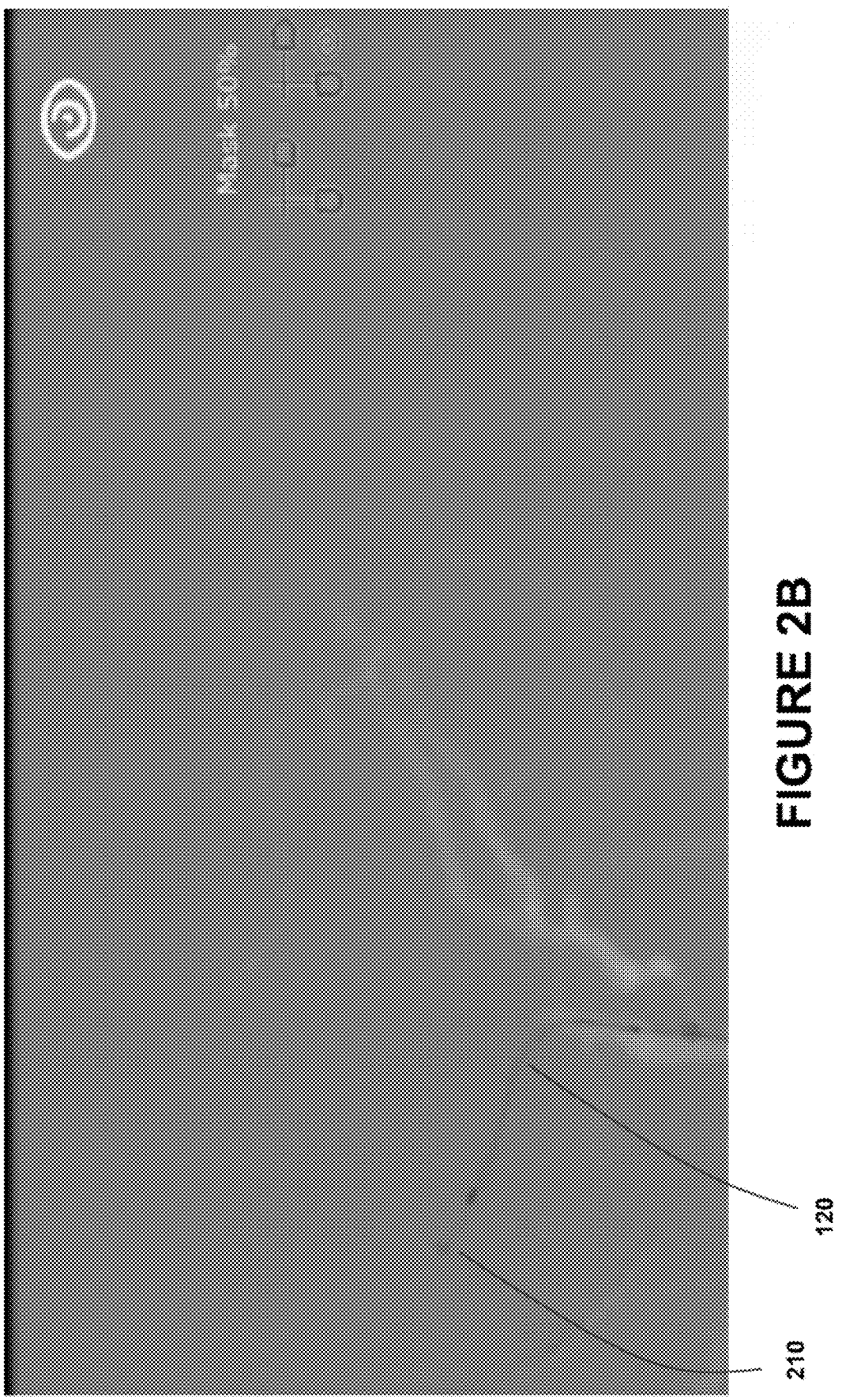
FIG. 2B is another exemplary x-ray image simulation that can be displayed by a feedback system in accordance with certain embodiments.

FIGS. 2A and 2B illustrate exemplary x-ray image simulations that can be displayed by the feedback system 130 while the simulated medical procedures are performed using the medical simulators 100. These figures show how the medical simulators can produce x-ray images of a human anatomy during the simulated medical procedures. FIG. 2A is a simulated x-ray image taken when the x-ray machine 150 is positioned above the head region of the simulation interface device 110. FIG. 2B is a simulated x-ray image that shows a tool 120 being threaded through an artery and releasing a stent retriever 210 into the artery.

In certain embodiments, the medical simulators 100 are configured with a training and assessment module that stores rules and other data for characterizing a mechanical thrombectomy procedure, monitoring the performance of the medical practitioners during a mechanical thrombectomy procedure, and providing information that assists the medical practitioners with developing and/or maintaining their skill sets for performing a mechanical thrombectomy procedure. The training and assessment module can be configured to, inter alia, define the procedural phases and sub-steps of the mechanical thrombectomy procedure, define a set of metrics to be tracked and monitored during the simulations of the mechanical thrombectomy procedure, determine if and when the phases and sub-steps of the mechanical thrombectomy procedure are completed during the simulations, detect when errors have occurred during the simulations of the mechanical thrombectomy procedure based on specified error criteria, compare the performance (e.g., including the monitored metrics) of medical practitioners to pre-defined benchmarks associated with the mechanical thrombectomy procedure, categorize the skill levels (e.g., novice, competent, expert, etc.) of the medical practitioners based on their performances during the mechanical thrombectomy simulations, and provide recommendations (e.g., such as recommended simulation exercises to enhance skills in certain areas) to assist the medical practitioners with advancing and/or maintaining their skillsets with respect to performing the simulated mechanical thrombectomy procedure. The discussion that follows describes how the training and assessment module can implement these functions for a mechanical thrombectomy procedure and other types of medical procedures.

As demonstrated in the tables below, a procedure which is the subject of a simulation can be divided into a plurality of phases (e.g., phases 1-N below), each of which includes one or more sub-steps (e.g., sub-steps 1-M below). The training and assessment module, which is stored in one or more computed storage devices of the medical simulators 100 (e.g., on a storage device integrated into the simulation interface devices 110), includes data and programming logic for defining each of these phases and determining whether or not the phases and/or sub-steps were completed during a simulation of the procedure. The tables below also identify exemplary errors (e.g., errors 1-P below) that can be monitored during each phase of the procedure. The training and assessment module also stores the data for defining and detecting errors that occur during each phase and/or sub-step. In certain embodiments, the functions of the training and assessment module (e.g., those related to determining whether phases and/or sub-steps were completed, detecting errors that occur during the simulations, and monitoring metrics during the simulations) can be performed by correlating the inputs received from a simulator (e.g., inputs received from sensors of the simulator indicating the movement of the tools 120 inside of the simulator) to the pre-stored data in the training and assessment module that is used to define the phases, sub-steps and errors and metrics.

For the sake of clarity, it is pointed out that the middle column in the upper portions of the tables below indicate that the training and assessment module stores information (e.g., a list of conditions) that can be used to determine whether or not the phases and sub-steps have been completed, as well as whether or not the phases and sub-steps are currently active (e.g., indicating that phase and/or sub-step is currently ongoing in a simulation). The middle column in the lower portions of the tables below indicates that errors are monitored during each phase and/or sub-step, and that the training and assessment module stores information for defining the errors. The numbers located to the left of each error description are identifiers that are used to identify the associated error. The same or similar errors can be monitored and detected throughout different phases and sub-steps. However, certain errors may be specific to particular phases and/or sub-steps. Further, the right column of the above tables (which is labeled "Earlier steps performed") includes numbers that identify one or more sub-steps that should be performed before the sub-step identified in the same row is performed. This is a powerful way of defining dependencies between steps and, in particular, the order in which the steps are to be performed. The training and assessment module can store and use this information to determine whether the phases and/or sub-steps are performed in an appropriate order during the simulations.

| Phase 1 | | |
|---|---|---|
| Phase I | Clinical High-Level Description of Phase<br>List of conditions that defines the Phase<br>(if conditions are met, then the phase is active) | Earlier steps performed |
| Sub-step 1.1 | Clinical Description of sub-step 1<br>List of conditions that defines the completion of the step | N/A |
| Sub-step 1.2 | Clinical Description of sub-step 2<br>List of conditions that defines the completion of the step | 1 |
| | Errors Monitored During Phase: | |
| Error ID #1.1 | Well defined conditions of a specific particular error occurring | |
| Error ID #1.2 | Well defined conditions of a specific particular error occurring | |
| Error ID #1.3 | Well defined conditions of a specific particular error occurring | |
| . . . | | |
| Error ID #1.P | Well defined conditions of a specific particular error occurring | |

| Phase N | | |
|---|---|---|
| Phase N | Clinical High-Level Description of Phase<br>A list of conditions defining the Phase. | Earlier steps performed |
| Sub-step N.1 | Clinical Description of sub-step N.1<br>List of conditions that defines the completion of the step | Any number(s) from 1 to M-1 |
| Sub-step N.2 | Clinical Description of sub-step N.2<br>List of conditions that defines the completion of the step | Any number(s) from 1 to M-1 |
| . . . | . . . | . . . |
| Sub-step N.M<br>(Any number of sub-steps can be included in each Phase) | Clinical Description of sub-step N.M<br>List of conditions that defines the completion of the step | Any number(s) from 1 to M-1 |
| | Errors Monitored During Phase: | |
| Error ID #N.1 | Well defined conditions of a specific particular error occurring | |
| Error ID #N.2 | Well defined conditions of a specific particular error occurring | |
| Error ID #N.3 | Well defined conditions of a specific particular error occurring | |
| Error ID #N.P | Well defined conditions of a specific particular error occurring | |

The phases, sub-steps and errors identified in the above tables illustrate an exemplary way of configuring aspects of the training and assessment module. It should be recognized that the phases, sub-steps and errors can be varied according to different embodiments.

For example, in the context of a simulation for a mechanical thrombectomy procedure for AIS, an initial phase may define the conditions and sub-steps associated with inserting a tool into a femoral artery, a plurality of middle phases may define the conditions and sub-steps associated with threading the tool up to a patient's brain and removing a blood clot, and an ending phase may define the conditions and sub-steps associated with removing the tool from the patient. As mentioned above, one or more errors may be associated with each phase and/or sub-step. For example, the errors monitored in this exemplary simulation may indicate whether certain anatomic components were inadvertently scraped or damaged, whether a tool used during the simulation was out of view, whether tools were pushed too far or excessive pressure was applied after resistance increased, whether tools were deployed in the wrong regions, and/or other similar types of errors.

As mentioned above, the training and assessment module of the medical simulators 100 may monitor various types of metrics during a simulation as discussed above. For example, the training and assessment module can be configured to monitor protocol adherence metrics, safety metrics, efficiency metrics, and precision metrics related to a mechanical thrombectomy procedure. Each of the metrics monitored during a mechanical thrombectomy simulation can be compared to pre-defined benchmarks that are stored in the training and assessment module. As mentioned above, this may involve associating a logical operator with each metric/benchmark pair to determine whether or not a benchmark was satisfied. The comparison of the monitored metrics and the benchmarks can be used to assess the performance of the medical practitioners performing the mechanical thrombectomy simulations.

The protocol adherence metrics can be used, inter alia, to determine whether a simulated procedure was performed according to best practices of a mechanical thrombectomy procedure, while the safety metrics can be used, inter alia, to monitor and determine whether the simulated mechanical thrombectomy procedure was performed in a manner that would cause risk to a patient and/or whether errors were committed during the simulated procedure. The efficiency metrics, inter alia, can be used to monitor and determine whether the simulated mechanical thrombectomy procedure was performed in an efficient manner. The tables below illustrate exemplary metrics (identified by the column labeled "Metric Id"), metric descriptions (identified by the column labeled "Metric"), operators (identified by the column labeled "Operator"), and benchmarks (identified by the column labeled "Benchmark") that can be used by the training and assessment module to assess a medical practitioner's performance during a simulated mechanical thrombectomy procedure. The tables below also include a column (labeled "Result") which indicates the results of a medical practitioner's performance during an exemplary simulation conducted for a mechanical thrombectomy procedure. The training and assessment module is configured to compare the computed results to the benchmarks using the operators in order to determine whether or not the benchmarks associated with the metrics have been satisfied.

The table below illustrates examples of cumulative or aggregated metrics that can be monitored throughout the entirety of a simulated mechanical thrombectomy procedure. These metrics represent exemplary efficiency metrics that can be monitored. As can be seen from the table further below, cumulative or aggregated metrics can also be monitored separately in each phase.

| Cumulative Metrics | | | | |
|---|---|---|---|---|
| Metric Id | Metric | Operator | Benchmark | Result |
| total_time | Total time | <= | 1369 s | 448 s |
| phases_finished | Phases finished | >= | 8 | 2 |
| steps_finished | Steps finished | >= | 36 | 6 |
| handling_errors | Number of handling errors | <= | 26 | 8 |
| total_syringe_volume | Contrast used | <= | 37.9 ml | 421.8 ml |
| fluoro_time | Total fluoroscope time | <= | 634 s | 243 s |
| cine_loop_time | Total cine time | <= | 7 s | 0 s |
| dsa_time | Total DSA time | <= | 31 s | 0 s |
| peak_skin_dose | Peak Skin Dose (Patient) | <= | 158.59 mGy | 22.72 mGy |
| reference_point_air_kerma | Reference Point Air Kerma (Patient) | <= | 259.24 mGy | 20.65 mGy |
| kerma_area_product | Kerma Area Product (Patient) | <= | 8.43 Gycm2 | 7.05 Gycm2 |
| equivalent_eye_dose | Eye Dose (Operator) | <= | 0.0226 mSv | 0.0035 mSv |
| equivalent_thyroid_dose | Thyroid Dose (Operator) | <= | 0.0226 mSv | 0.0041 mSv |

The table below illustrates examples of metrics that can be monitored during each phase and/or sub-step of a simulated mechanical thrombectomy procedure. The metrics in this table include protocol adherence metrics (e.g., "Steps finished"), safety metrics (e.g., "phase_id_I_step_id_1"), and efficiency metrics (e.g., "Total time").

| Phase 1-N Metrics | | | | |
|---|---|---|---|---|
| Metric Id | Metric | Operator | Benchmark | Result |
| phase_id_I_metric_id_total_time | Total time | <= | 68 s | 52 s |
| phase_id_I_metric_id_steps_finished | Steps finished | >= | 2 | 2 |
| phase_id_I_metric_id_handling_errors | Number of handling errors | <= | 0 | 1 |

-continued

| Phase 1-N Metrics | | | | |
|---|---|---|---|---|
| Metric Id | Metric | Operator | Benchmark | Result |
| phase_id_I_metric_id_total_syringe_volume | Contrast used | <= | 0.0 ml | 0.0 ml |
| phase_id_I_metric_id_fluoro_time | Total fluoroscope time | <= | 50 s | 49 s |
| phase_id_I_metric_id_cine_loop_time | Total cine time | <= | 0 s | 0 s |
| phase_id_I_metric_id_dsa_time | Total DSA time | <= | 0 s | 0 s |
| phase_id_I_metric_id_peak_skin_dose | Peak Skin Dose (Patient) | <= | 16.07 mGy | 9.52 mGy |
| phase_id_I_metric_id_reference_point_air_kerma | Reference Point Air Kerma (Patient) | <= | 19.99 mGy | 8.81 mGy |
| phase_id_I_metric_id_kerma_area_product | Kerma Area Product (Patient) | <= | 3.87 Gycm2 | 3.01 Gycm2 |
| phase_id_I_metric_id_equivalent_eye_dose | Eye Dose (Operator) | <= | 0.0018 mSv | 0.0018 mSv |
| phase_id_I_metric_id_equivalent_thyroid_dose | Thyroid Dose (Operator) | <= | 0.0018 mSv | 0.0018 mSv |
| phase_id_I_metric_id_equivalent_gonad_dose | Gonad Dose (Operator) | <= | 0.0104 mSv | 0.0125 mSv |
| phase_id_I_step_id_1 | Specific task performed | = | passed | passed |
| phase_id_I_step_id_2 | Specific task performed | = | passed | passed |
| phase_id_I_error_id_1 | Specific error occurrence | <= | 0 | 0 |
| phase_id_I_error_id_2 | Specific error occurrence | <= | 0 | 1 |
| phase_id_I_error_id_3 | Specific error occurrence | <= | 0 | 0 |
| ... | ... | ... | ... | ... |
| phase_id_I_error_id_N | Specific error occurrence | <= | 0 | 0 |

The metrics identified in the above are examples of metrics that can be defined by the training and assessment module and monitored during the simulations. However, it should be recognized that other types of metrics may also be defined and monitored.

Figure 3:
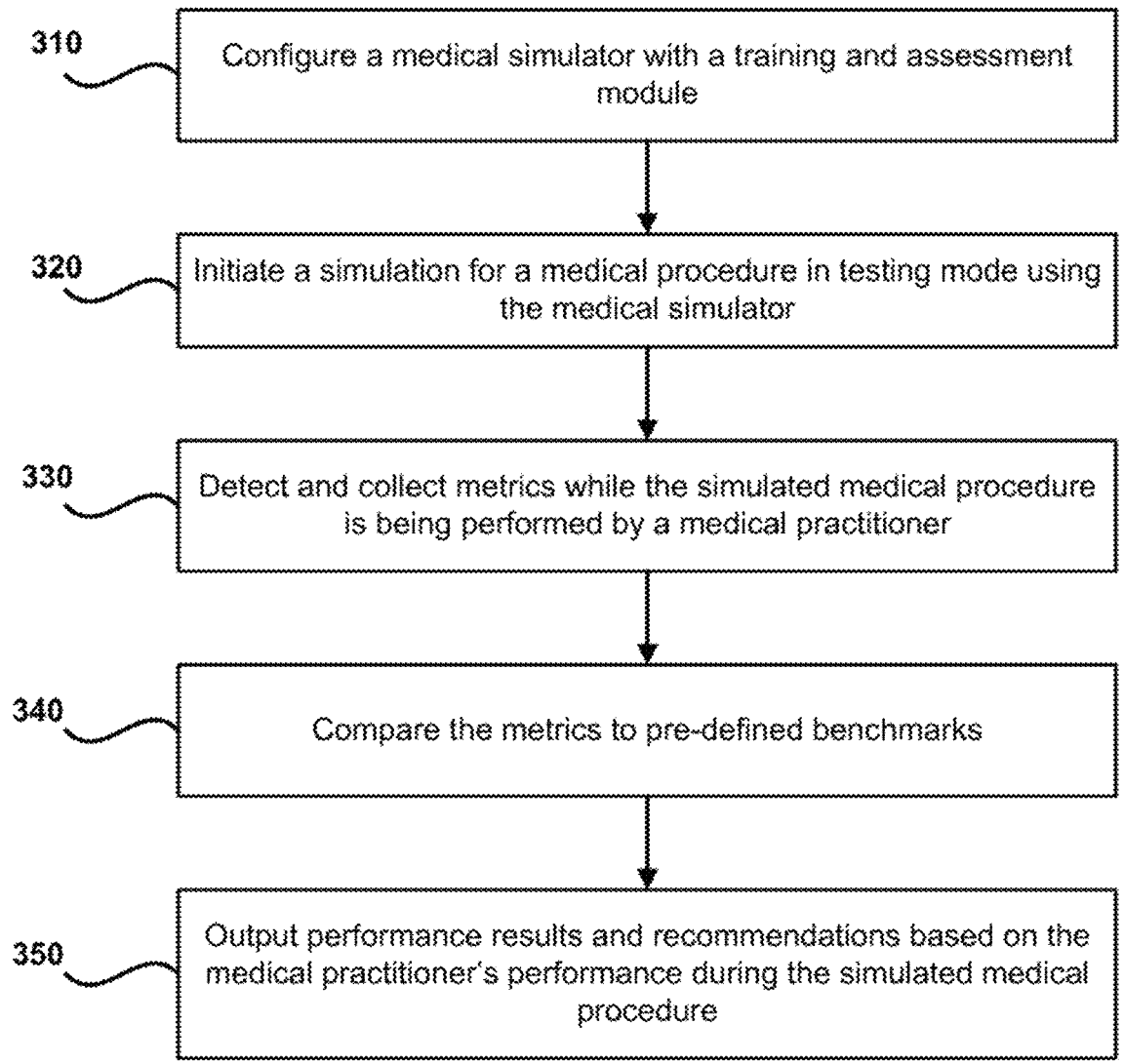
FIG. 3 is a flow chart that discloses an exemplary method for using a medical simulator to conduct a simulation in testing mode in accordance with certain embodiments.

FIG. 3 is a flow chart that discloses a method 300 for using a medical simulator to conduct a simulation in testing mode in accordance with certain embodiments. In certain embodiments, the method 300 may be executed by any of the medical simulators 100 illustrated in FIGS. 1A-1D or any other suitable medical simulator, such as the ones discussed above.

In step 310, a medical simulator 100 is configured with a training and assessment module. The training and assessment module can define the phases, sub-steps, errors, metrics and benchmarks for performing one or more medical procedures. In certain embodiments, the benchmarks are established during a calibration phase of the medical simulator 100 in which metrics of experts performing the simulated procedures are tracked and used to set the benchmarks.

In step 320, a simulation for a medical procedure is initiated in testing mode using the medical simulator 100. The medical simulator generally can be configured to simulate any type of medical procedure suitable for simulation using medical simulator 100. In certain exemplary embodiments discussed herein, the medical simulator is configured to simulate a mechanical thrombectomy procedure (e.g., to treat a patient who has experienced an AIS).

In step 330, metrics are detected, computed, and collected while the medical procedure is being performed by a medical practitioner on the medical simulator 100. The medical simulator 100 can be equipped with various sensors that can be utilized to generate at least a portion of the metrics, either directly (e.g., based on the actual outputs of the sensors) or indirectly (e.g., by using the using the processors to compute the metrics based on the outputs of the sensors). For example, as one or more tools 120 are inserted into a simulation interface device 110 of the medical simulator 100, the sensors of the medical simulator can monitor the movement (e.g., rotational movement, translation movement, pressure applied, etc.) of the tools and other activities that are conducted as part of the simulation (e.g., the use of x-ray imaging equipment and timing aspects). Various metrics can be derived from monitoring and tracking this information. Exemplary metrics may include the protocol adherence metrics, safety metrics, efficiency metrics, and precision metrics described above.

In step 340, the metrics are compared to pre-defined benchmarks. The benchmarks can be used to determine whether a medical practitioner's performance during a simulation was proficient for a variety of different aspects. Each benchmark may be associated with a logical operator which is used to facilitate the comparison of the measured metric with the pre-defined benchmark.

In step 350, performance results and recommendations are output based on the medical practitioner's performance during the simulated medical procedure. The results and recommendations may be displayed on the feedback system 130. The results and recommendations can also be printed, e-mailed and/or output in other ways. The results of the simulation may provide an assessment to indicate how well the medical practitioner performed during the simulations (e.g., based on a comparison of the measured metrics to the pre-defined benchmarks). The result of the assessment can identify areas of improvement for the medical practitioner and can recommend exercises that explicitly address the areas requiring improvement. As an example, if the result of an assessment shows inefficient use of x-ray imaging (e.g., unnecessarily high radiation exposure for the patient), then the medical practitioner can be directed to a specific training module that is configured to improve the medical practitioner's use of x-ray imaging during a specific medical procedure. Other training modules may be stored and made available to hone other types of skills.

Figure 4:
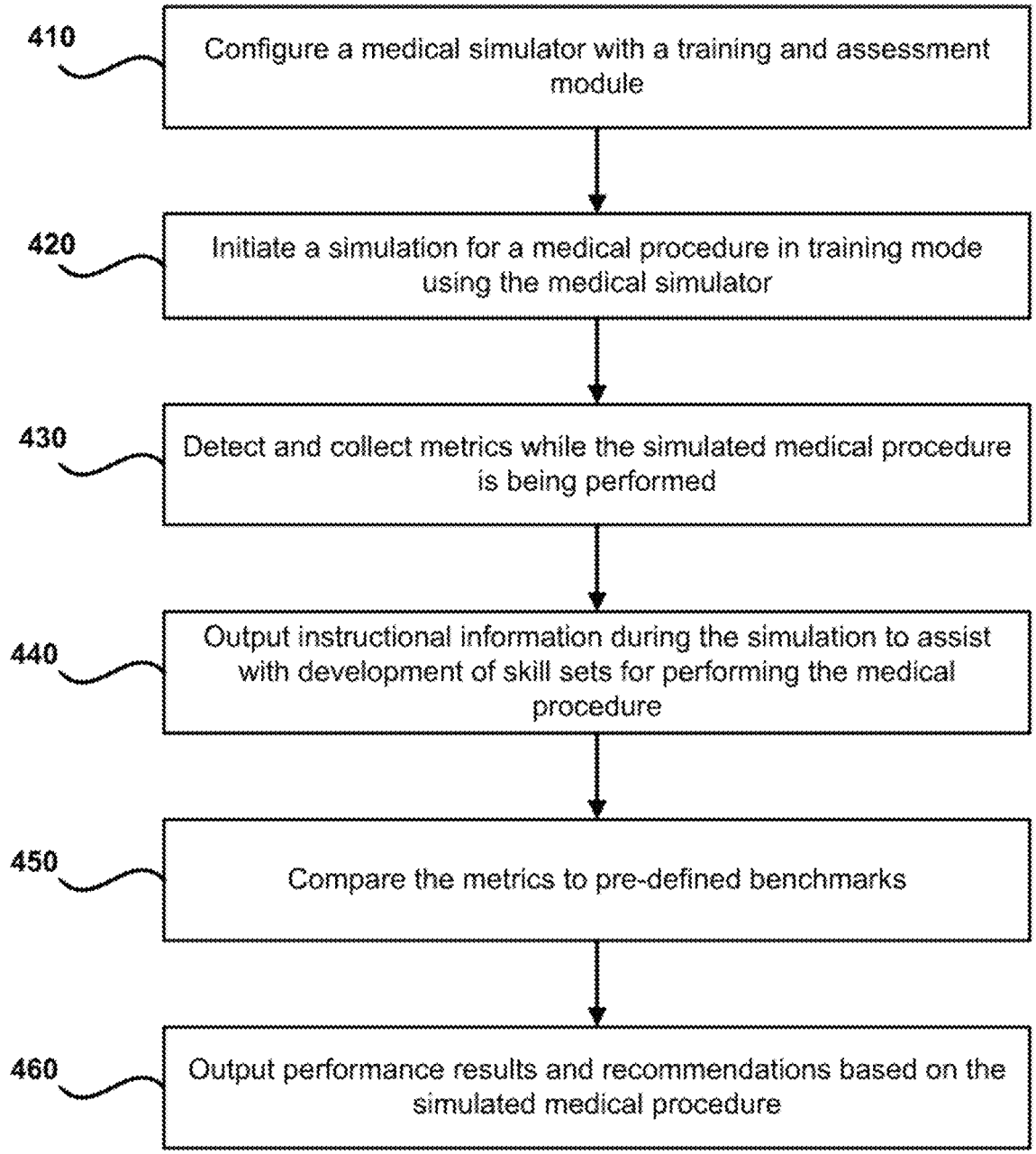
FIG. 4 is a flow chart that discloses an exemplary method 400 using a medical simulator to conduct a simulation in training mode in accordance with certain embodiments.

FIG. 4 is a flow chart that discloses a method 400 for using a medical simulator to conduct a simulation in training mode in accordance with certain embodiments. In certain embodiments, the method 400 may be executed by any of the medical simulators 100 illustrated in FIGS. 1A-1D or any other suitable medical simulator, such as the ones discussed above.

In step 410, a medical simulator 100 is configured with a training and assessment module. As mentioned above, the training and assessment module can define the phases, sub-steps, errors, metrics and benchmarks for performing one or more medical procedures. The training and assessment module also stores data and information that can be useful in training medical practitioners to perform medical procedures.

In step 420, a simulation for a medical procedure is initiated in training mode using the medical simulator 100. In training mode, the simulation is adapted to provide assistance to the medical practitioner during the simulations. The medical simulator generally can be configured to execute a simulation for any type of medical procedure. As mentioned above, the medical simulator may be configured to simulate a mechanical thrombectomy procedure (e.g., to treat a patient who has experienced an AIS) in certain exemplary embodiments. Also as mentioned above, the principles described herein can be adapted for other medical procedure simulations.

In step 430, metrics are detected, computed, and collected during the simulation. This step can be performed in the same manner as described above with respect to step 330.

In step 440, instructional information is output during the simulation to assist with development of skill sets for performing the medical procedure. The instructional information can be output by audio/video devices, or other output devices, included in the feedback system. The instructional information can include any type of data that assists medical practitioners with learning how to execute the medical procedure. Exemplary instructional information includes, but is not limited to, the following: error messages identifying when errors are committed during the simulations; warning messages indicating that errors are close to being committed; information that indicates how particular steps of the medical procedures are to be performed; information that identifies tools to be used during the simulations and how the tools should be used; information that indicates how imaging systems and modalities should be used during the simulations; recommendations to perform particular training modules to enhance certain skill sets; and other related information.

Steps 450 and 460 can be performed in the same manner as described above with respect to steps 440 and 450, respectively.

Figure 5:
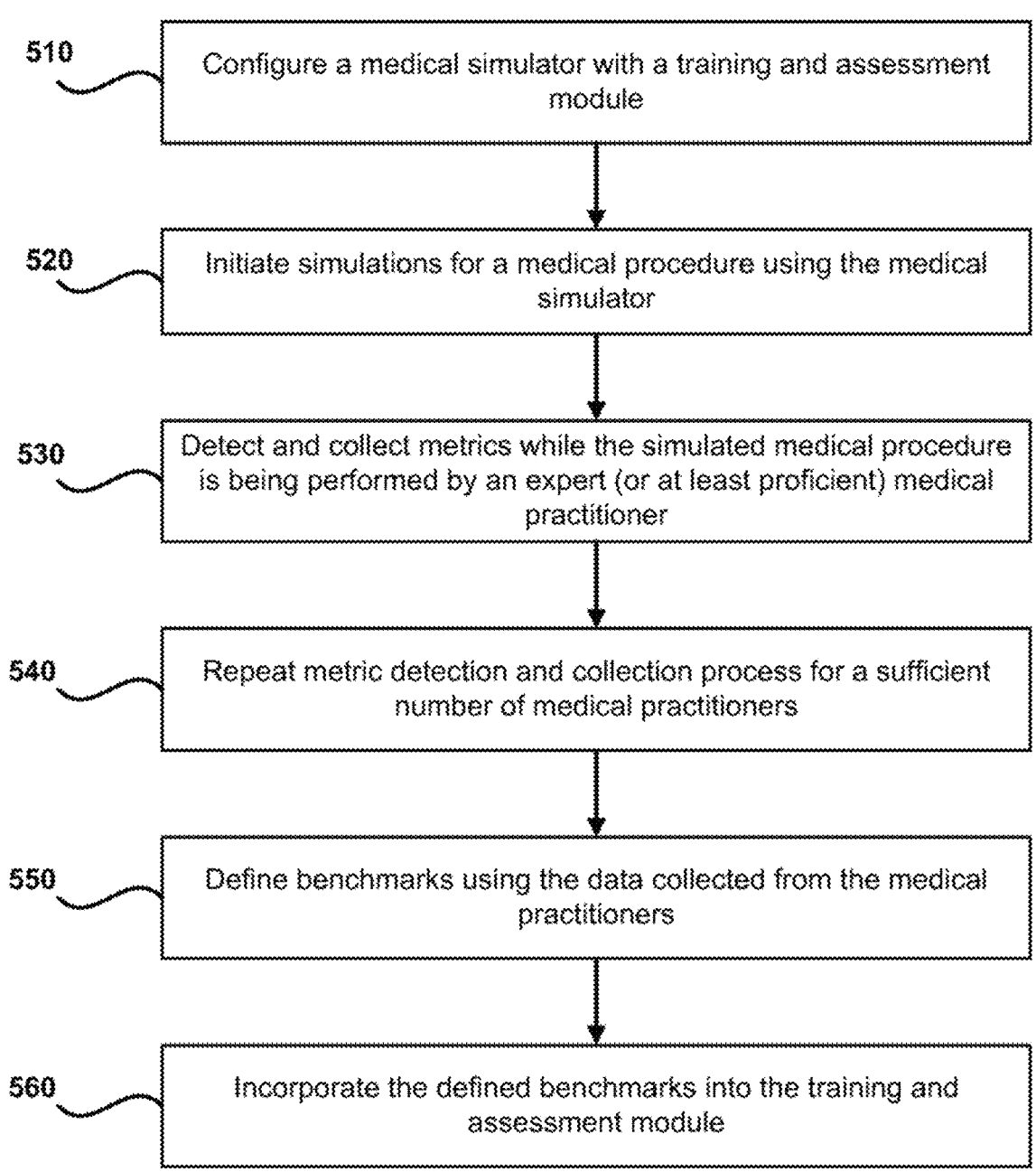
FIG. 5 is a flow chart that discloses an exemplary method for establishing benchmarks for use in a simulation in accordance with certain embodiments.

FIG. 5 is a flow chart that discloses a method 500 for establishing benchmarks for use in a simulation in accordance with certain embodiments. In certain embodiments, the method 500 may be executed by any of the medical simulators 100 illustrated in FIGS. 1A-1D or any other suitable medical simulator, such as the ones discussed above.

In step 510, a medical simulator 100 is configured with a training and assessment module. In step 520, simulations for a medical procedure are initiated using the medical simulator 100. In step 530, metrics are detected, computed and collected while the simulated medical procedure is being performed by an expert (or at least proficient) medical practitioner or user. In step 540, the metric detection, computation and collection process is repeated for a sufficient number of medical practitioners. In step 550, benchmarks for the simulation of the medical procedure are defined using the data collected from the medical practitioners. For example, a benchmark may be established for each metric by averaging the recorded metrics of the medical practitioners, or may be established in other ways. In step 560, the benchmarks are incorporated into the training and assessment module. The training and assessment module can thereafter use the benchmarks to determine whether trainees participating in the simulations are performing aspects of the simulated medical procedures proficiently.

Figure 6:
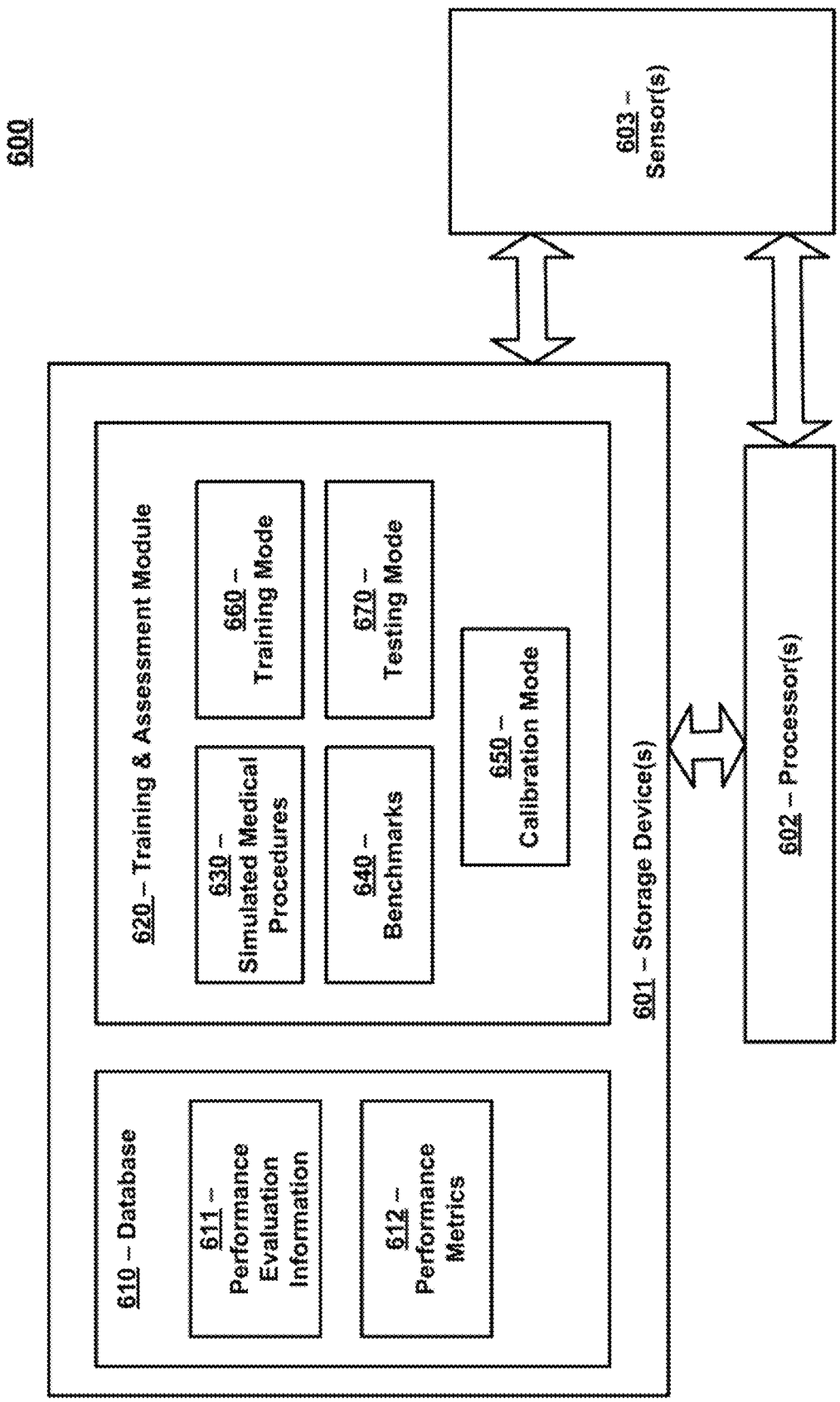
FIG. 6 is a block diagram of an exemplary system in accordance with certain embodiments.

FIG. 6 is a block diagram of a medical simulation system 600 in accordance with certain embodiments. The medical simulation system 600 includes one or more storage devices 601, one or more processors 602, and one or more sensors 603 that are in communication with each other. The one or more storage devices 601 can include: i) non-volatile memory, such as, for example, read only memory (ROM) or programmable read only memory (PROM); and/or (ii) volatile memory, such as, for example, random access memory (RAM), dynamic RAM (DRAM), static RAM (SRAM), etc. In these or other embodiments, storage devices 601 can comprise (i) non-transitory memory and/or (ii) transitory memory. The one or more processors 602 can include one or more central processing units (CPUs), graphical processing units (GPUs), controllers, microprocessors, digital signal processors, and/or computational circuits. The one or more storage devices 601 can store data and instructions associated with one or more databases 610 and a training and assessment module 620 that comprises one or more simulated medical procedures 630, one or more benchmarks 640, a calibration mode 650, a training mode 660, and a testing mode 670. The one or more processors 602 are configured to execute instructions associated with these and other components. Each of these components is described in further detail below.

In certain embodiments, the one or more sensors 603 may be integrated into any of the simulation interface devices mentioned in this disclosure and/or other simulation interface devices. The one or more sensors 603 may be utilized to monitor usage of the medical tools (e.g., wires, catheters, stents, etc.) by the medical practitioners performing the medical procedures, the medical practitioners' performance when performing the simulated medical procedures, and/or other aspects of the performance. The sensors 603 may be configured to generate signals indicating positions and movements of the medical tools within the simulation interface devices. The information generated by the sensors 603 may be utilized to determine whether the medical tools contacted various anatomic components (e.g., blood vessels, organs, tissues, veins, arteries, etc.) of a simulated anatomy during the medical practitioners' performance of the procedures, and whether the medical tools were appropriately manipulated by the medical practitioners performing the medical procedures. Any appropriate sensor may be utilized 603 to perform these and other functions. For example, in certain embodiments, the sensors 603 may include pressure sensors, haptic sensors, video sensors, force gauges, proximity sensors, and/or other types of sensors.

The training and assessment module 620 stores instructions, code, information, and/or other data associated with implementing one or more simulated medical procedures 630. The instructions, code information, and/or other data associated with each of the simulated medical procedures 630 can define the phases, steps, tasks, errors, benchmarks 640, appropriate tool usage, and/or other related information associated with simulated medical procedures 630. In certain embodiments, the training and assessment module 620 is configured to implement a simulated medical procedure 630 for a mechanical thrombectomy procedure (e.g., which can be used to treat a blood clot resulting from AIS). The training and assessment module 620 can additionally, or alternatively, be configured to execute other types of simulated medical procedures 630 including, but not limited to, other types of simulated endovascular medical procedures and other types of clinical procedures.

Each of the simulated medical procedures 630 can be associated with a set of benchmarks 640. The benchmarks 640 can define values that are used to determine whether a medical practitioner performing a simulated medical procedure 630 satisfied particular requirements or aspects of the medical procedure. For example, the benchmarks 640 may indicate acceptable values corresponding to any of the protocol adherence metrics, safety metrics, efficiency metrics, and/or precision metrics mentioned in this disclosure. Appropriate benchmarks 640 can be provided for other types of metrics as well.

For each simulated medical procedure 630 that is made available, the training and assessment module 620 can be configured to operate in various modes including, but not limited to, a calibration mode 650, a training mode 660, and a testing mode 670. The calibration mode 650 can be utilized to establish the benchmarks 640 and other settings for each of the simulated medical procedures. This may be performed in accordance with the method 500 of FIG. 5 and/or in other ways. In the training mode 660, the training and assessment module 620 is configured to provide live feedback and guidance throughout the procedure (e.g., by notifying the medical practitioners of any errors committed and guiding the medical practitioners throughout the phrases and tasks associated with the simulated medical procedures 630). For example, proximal feedback may be provided in the form of visual, auditory or haptic cues to a trainee when errors are committed, or when tasks and steps are not correctly finished in the correct order. This may be performed in accordance with the method 400 of FIG. 4 and/or in other ways. In the testing mode 670, some or all of the training assistance is turned off or deactivated, and the medical practitioners are permitted to perform the simulated medical procedures 630 on their own without guidance or assistance.

During the simulated medical procedures 630, performance metrics 612 may be derived and/or computed related to a medical practitioner's performance. Some of the performance metrics 612 may be based on signals or parameters generated directly by the sensors 603 or indirectly computed by the processors 602 as part of the simulated procedure. For example, in certain embodiments, one or more performance metrics 612 may be generated in real-time by the sensors 603 as the medical practitioner is performing the simulated medical procedures 630. Other performance metrics 612 may be based on the medical practitioner's adherence to protocols for the simulated medical procedures (e.g., timely performance of the simulated medical procedures and/or sub-steps associated with the simulated medical procedures) and may be computed by the processors 602 as part of the simulated procedure. The performance metrics 612 can reflect a medical practitioner's performance during a medical procedure 630 in various ways. For example, as explained above, the performance metrics 612 may reflect the medical practitioner's performance with regards to any protocol adherence metrics, safety metrics, efficiency metrics, precision metrics, and/or other metrics mentioned in this disclosure. The monitored performance metrics 612 may be compared to the pre-defined benchmarks 640 established during the calibration mode 650 to assess the medical practitioner's performance during the simulated medical procedures 630.

Performance evaluation information 611 may be generated based on medical practitioners' performance during the simulated medical procedures 630. The performance evaluation information 611 can generally include any data, information, and/or feedback associated with the medical practitioners' performance. For example, the performance evaluation information 611 can include: information that identifies skills that could use improvement; information that identifies skills in which the medical practitioner has shown proficiency; recommendations for simulated exercises to assist with developing and/or maintaining certain skills; summaries of performance metrics 612 (e.g., including a breakdown of metrics that shows whether or not each of performance metrics 612 satisfied corresponding benchmarks 640); information that identifies whether or not tools were appropriately utilized and/or controlled during the simulated medical procedures 630); information that indicates whether or not the phases and sub-steps of the medical procedures 630 were completed during the simulated medical procedures 630; information that indicates whether or not the phases and sub-steps of the medical procedures 630 were completed in an appropriate order during the simulated medical procedures 630; information that identifies any errors that were detected during the simulated medical procedures 630; information indicating whether or not protocol adherence metrics, safety metrics, efficiency metrics, and/or other performance metrics 612 were satisfied; and/or any other information related to the simulated medical procedures 630.

In certain embodiments, some or all of the benchmarks 640 corresponding to the various metrics being monitoring may be based on a mean value or average value that is derived during a calibration mode 650 based on performances of the simulated medical procedures 630 by skilled medical practitioners or operators. The performance evaluation information 611 generated for a simulated medical procedure 630 may express a medical practitioner's performance, at least in part, by computing a standard deviation from these benchmarks 640.

After performing a simulated medical procedure 630, the performance evaluation information 611 corresponding to the simulated medical procedure 630 may be provided to a medical practitioner (and/or other individuals) that performed the simulated medical procedure 630. The performance evaluation information 611 may be output on a feedback system and/or provided in other ways (e.g., via an e-mail, inbox, and/or online account).

In certain embodiments, the performance evaluation information 611 can include one or more recommendations for simulated exercises and/or training activities that can be performed on the medical simulators. The recommended exercises and/or training activities can be provided using an iterative training model that assists the medical practitioners with reaching and/or maintaining a certain level of proficiency. For example, recommended exercises and/or training activities can be made available with varying levels of difficulty and/or varying levels of guidance. As a novice or non-expert medical practitioner's skills improve, the medical practitioner can be provided with exercises and/or training exercises having increased difficulty and/or less instructional guidance. By gradually increasing the difficulty and/or reducing the guidance provided, the medical practitioner can advance to difficult skill levels (e.g., novice, competent, expert, etc.), each of which may be associated with a different set of exercises and training activities.

It should be understood that exemplary embodiments described above are not intended to be limiting and that the inventive techniques described herein can be used in many other scenarios as well. It should also be further understood that the configurations and structures of the system components in FIGS. 1A-1D and 6 can vary according to different embodiments. For example, while certain components or sub-components may be depicted as being distinct or separate from one another, it should be recognized that this distinction may be a logical distinction rather than a physical or actual distinction. Any or all of the components and sub-components can be combined with one another to perform the functions described herein, and any aspect or feature that is described as being performed by one component or sub-component can be performed by any or all of the other components and sub-components. Likewise, although certain figures may depict a specific number of each component (e.g., a single simulation interface device 110, a single tool 120, a single feedback system 130, etc.), this is not intended to be limiting and the system can include any number of each such component.

In view of the above, the medical simulators described herein enable medical practitioners to perform medical procedures in a simulated environment. The feedback system provides a visualization of the simulated environment during the performance of the medical procedures by the medical practitioners (e.g., by showing a simulated anatomy and tools being manipulated in the simulated anatomy) and corresponds to what is visualized when performing a real procedure on a real patient. The training and assessment module evaluates the actions performed by the medical practitioners during the medical procedures, and can generate guidance, instructions, and recommendations to improve the medical practitioners' performance of the medical procedures. As a result, medical practitioners can improve or maintain their skill sets by actually performing the medical procedures in virtual environments and without imposing risks on living patients.

In certain embodiments, a system is provided for assessing an operator's performance of a clinical procedure using a medical simulator. The system includes: a simulation interface device comprising a physical assembly that includes one or more sensors configured to generate monitored parameters related to an operator's manipulation of one or more medical tools within the physical assembly during a simulated medical procedure; one or more computing devices comprising one or more processors and one or more non-transitory storage devices for storing instructions, wherein execution of the instructions by the one or more processors causes the one or more computing devices to: receive, during the simulated medical procedure, the monitored parameters generated directly by the one or more sensors or indirectly computed by the one or more processors as part of the simulated procedure; detect information pertaining to the operator's adherence with a defined protocol for the simulated medical procedure; provide simulation metrics based on the detected information and the monitored parameters; compare the simulation metrics with pre-defined benchmarks, the pre-defined benchmarks at least including information that is used to assess the operator's proficiency with respect to executing tasks associated with performing the simulated medical procedure, using the one or more medical tools during the simulated medical procedure, and avoiding errors associated with performing the simulated medical procedure; and generate, based at least in part on the comparison of the simulation metrics with the pre-defined benchmarks, performance evaluation information related to the operator's performance during the simulated medical procedure.

In certain embodiments, a method is provided for assessing an operator's performance of a clinical procedure using a medical simulator. The method comprises: receive, during a simulated medical procedure, monitored parameters generated directly by the one or more sensors included in a physical assembly of a simulation interface device or indirectly computed by the one or more processors as part of the simulated procedure, the monitored parameters directly or indirectly relating to an operator's manipulation of one or more medical tools within the physical assembly during the simulated medical procedure; detect information pertaining to the operator's adherence with a defined protocol for the simulated medical procedure; provide simulation metrics based on the detected information and the monitored parameters; compare the simulation metrics with pre-defined benchmarks, the pre-defined benchmarks at least including information that is used to assess the operator's proficiency with respect to executing tasks associated with performing the simulated medical procedure, using the one or more medical tools during the simulated medical procedure, and avoiding errors associated with performing the simulated medical procedure; and generate, based at least in part on the comparison of the simulation metrics with the pre-defined benchmarks, performance evaluation information related to the operator's performance during the simulated medical procedure.

In certain embodiments, a system is provided for assessing an operator's performance of a medical procedure using a medical simulator. The system comprises: a simulation interface device comprising a physical assembly that includes one or more sensors configured to generate parameters related to an operator's manipulation of one or more medical tools within the physical assembly when performing a medical procedure; one or more computing devices comprising one or more processors and one or more non-transitory storage devices for storing instructions, wherein execution of the instructions by the one or more processors causes the one or more computing devices to: receive, during performance of the medical procedure by the operator, the parameters generated directly or indirectly when fed through the procedure simulation by the one or more sensors; derive performance metrics associated with the operator's performance of the medical procedure, wherein at least a portion of the performance metrics are based on the parameters generated directly or indirectly when fed through the procedure simulation by the one or more sensors; compare the performance metrics with predefined benchmarks that are utilized to assess the operator's performance; and generate, based at least in part on the comparison of the performance metrics with the predefined benchmarks, performance evaluation information related to the operator's performance during the medical procedure.

In certain embodiments, a method is provided for assessing an operator's performance of a medical procedure using a medical simulator. The method comprises: receiving, during a medical procedure performed, parameters generated directly or indirectly when fed through the procedure simulation by one or more sensors included in a physical assembly of a simulation interface device, the parameters relating to an operator's manipulation of one or more medical tools within the physical assembly during the simulated medical procedure; deriving performance metrics associated with the operator's performance of the medical procedure, wherein at least a portion of the performance metrics are derived using the parameters generated directly or indirectly when fed through the procedure simulation by the one or more sensors; comparing the performance metrics with predefined benchmarks that are utilized to assess the operator's performance; and generating, based at least in part on the comparison of the performance metrics with the predefined benchmarks, performance evaluation information related to the operator's performance during the medical procedure.

Accordingly, while various novel features of the invention have been shown, described and pointed out as applied to particular embodiments thereof, it should be understood that various omissions and substitutions and changes in the form and details of the systems and methods described and illustrated, may be made by those skilled in the art without departing from the spirit of the invention. Amongst other things, the steps of the methods may be carried out in different orders in many cases where such may be appropriate. Those skilled in the art will recognize, based on the above disclosure and an understanding therefrom of the teachings of the invention, that the particular hardware and devices that are part of the system described herein, and the general functionality provided by and incorporated therein, may vary in different embodiments of the invention. Accordingly, the particular system components are for illustrative purposes to facilitate a full and complete understanding and appreciation of the various aspects and functionality of particular embodiments of the invention as realized in system and method embodiments thereof. Those skilled in the art will appreciate that the invention can be practiced in other than the described embodiments, which are presented for purposes of illustration and not limitation.

What is claimed is:

1. A system for assessing an operator's performance of a simulated medical procedure, the system comprising:
   a simulation interface device comprising a physical assembly that includes one or more sensors configured to generate parameters related to an operator's manipulation of one or more medical tools within the physical assembly when performing a simulated medical procedure; and
   simulation software stored on one or more non-transitory storage devices and executed by one or more processors;
   wherein the simulation software stores one or more data structures for defining the simulated medical procedure, the one or more data structures including:
      (i) phase data defining a plurality of phases in the simulated medical procedure, wherein the phase data includes a first list of conditions defining when each of the phases is active;
      (ii) sub-step data defining one or more sub-steps for each of the plurality of phases in the simulated medical procedure, wherein the sub-step data includes a second list of conditions defining when each of the sub-steps is active;
      (iii) dependency data defining an order in which the one or more sub-steps is performed, wherein the dependency data is stored for each sub-step; and
      (iv) predefined benchmarks utilized to assess the operator's performance, each of the predefined benchmarks including an identifier, a mathematical operator, and a benchmark value; and
   wherein, to assess the operator's performance of the simulated medical procedure, the simulation software is configured to:
      determine, based on the first list of conditions or the second list of conditions, which of the phases or sub-steps is active during the operator's performance of the simulated medical procedure;
      derive performance metrics associated with the operator's performance of the simulated medical procedure based, at least in part, on the parameters generated by the one or more sensors, the performance metrics including a first performance metric derived based on the operator's compliance with the dependency data;
      compare at least one of the performance metrics with the predefined benchmarks using a result value derived using the parameters generated by the one or more sensors, the mathematical operator, and the benchmark value; and
      generate, based, at least in part, on the comparison of the performance metrics with the predefined benchmarks, performance evaluation information related to the operator's performance during the simulated medical procedure.

2. The system of claim 1, further comprising:
   a simulated imaging feed output display updated in real-time throughout the simulated medical procedure to reflect movements of the one or more medical tools within the physical assembly of the simulation interface device, wherein the movements of the one or more medical tools within the physical assembly are translated into movements of the one or more medical tools within a computer-simulated human anatomy.

3. The system of claim 2, wherein, throughout the simulated medical procedure, the simulation software utilizes the parameters generated by the one or more sensors to simultaneously track in parallel the performance metrics and provide real-time imaging guidance to the operator via the simulated imaging feed output display.

4. The system of claim 1, wherein the predefined benchmarks are utilized to evaluate the operator's performance with respect to:
   protocol adherence metrics indicating whether tasks associated with performing the simulated medical procedure were correctly completed, and whether the tasks were performed in an appropriate order;
   safety metrics indicating whether usage of the one or more medical tools during the simulated medical procedure resulted in errors corresponding to one or more potential health risks;
   efficiency metrics indicating whether the simulated medical procedure, or the tasks associated with the simulated medical procedure, is performed in an efficient fashion as defined by the predefined benchmarks; and
   precision metrics indicating whether the simulated medical procedure, or the tasks associated with the simulated medical procedure, is performed by the operator with a level of precision as defined by the predefined benchmarks.

5. The system of claim 1, wherein the one or more sensors include one or more pressure-measuring sensors and the parameters generated by the pressure-measuring sensors are utilized to evaluate whether excessive pressure was applied as defined by the predefined benchmarks.

6. The system of claim 1, wherein:
the phase data defining the plurality of phases includes a first simulation phase, a second simulation phase, and a third simulation phase;
wherein the phase data further includes:
  one or more conditions defining when the first simulation phase is active;
  one or more conditions defining when the second simulation phase is active; and
  one or more conditions defining when the third simulation phase is active;
the sub-step data for each of the plurality of phases in the simulated medical procedure links or associates each the sub-steps with one of the plurality of phases;
the one or more data structures defining the simulated medical procedure further includes error condition data for each of the of the plurality of phases, wherein:
  the error condition data defines a third list of conditions for detecting occurrences of errors during the simulated medical procedure and the third list of conditions includes:
    one or more conditions defining when an error has occurred during the first simulation phase;
    one or more conditions defining when an error has occurred during the second simulation phase; and
    one or more conditions defining when an error has occurred during the third simulation phase; and
the error condition data for each of the plurality of phases links or associates each of the third list of conditions to at least one of the plurality of phases.

7. The system of claim 6, wherein:
to assess the operator's performance of the simulated medical procedure, the simulation software is further configured to:
  access the phase data stored in the one or more data structures to determine when the first simulation phase, the second simulation phase, and the third simulation phase become active;
  access the sub-step data stored in the one or more data structures to determine when each of the plurality of sub-steps become active; and
  access the error condition data stored in the one or more data structures to detect error occurrences during the simulated medical procedure.

8. The system of claim 1, wherein:
the simulation software enables a plurality of simulated medical procedures to be performed; and
  for each of the plurality of simulated medical procedures, the simulation software stores different phase data, different sub-step data, different dependency data, and different benchmark data.

9. The system of claim 1, wherein the one or more data structures include one or more tables.

10. The system of claim 1, wherein the benchmark value is updated based on a plurality of simulation results, wherein each one of the plurality of simulation results is a result of a simulation performed by a medical practitioner.

11. A method for assessing an operator's performance of a simulated medical procedure, the method comprising:
  generating, using a simulation interface device comprising a physical assembly that includes one or more sensors, parameters related to an operator's manipulation of one or more medical tools within the physical assembly when performing a simulated medical procedure; and
  executing, by one or more processors, simulation software stored on one or more non-transitory storage devices;
  storing, by the simulation software, one or more data structures for defining the simulated medical procedure, the one or more data structures including:
    (i) phase data defining a plurality of phases in the simulated medical procedure, wherein the phase data includes a first list of conditions defining when each of the phases is active;
    (ii) sub-step data defining one or more sub-steps for each of the plurality of phases in the simulated medical procedure, wherein the sub-step data includes a second list of conditions defining when each of the sub-steps is active;
    (iii) dependency data defining an order in which the one or more sub-steps is performed, wherein the dependency data is stored for each sub-step; and
    (iv) predefined benchmarks utilized to assess the operator's performance, each of the predefined benchmarks including an identifier, a mathematical operator, and a benchmark value; and
  wherein, during the operator's performance of the simulated medical procedure, the simulation software is configured to assess the operator's performance, at least in part, by:
    determining, based on the first list of conditions or the second list of conditions, which of the phases or sub-steps is active during the operator's performance of the simulated medical procedure;
    deriving performance metrics associated with the operator's performance of the simulated medical procedure based, at least in part, on the parameters generated by the one or more sensors, the performance metrics including a first performance metric derived based on the operator's compliance with the dependency data;
    comparing at least one of the performance metrics with the predefined benchmarks using a result value derived using the parameters generated by the one or more sensors, the mathematical operator, and the benchmark value; and
    generating, based, at least in part, on the comparison of the performance metrics with the predefined benchmarks, performance evaluation information related to the operator's performance during the simulated medical procedure.

12. The method of claim 11, further comprising:
updating, in real-time, throughout the simulated medical procedure, a simulated imaging feed output display to reflect movements of the one or more medical tools within the physical assembly of the simulation interface device, wherein the movements of the one or more medical tools within the physical assembly are translated into movements of the one or more medical tools within a computer-simulated human anatomy.

13. The method of claim 12, wherein, throughout the simulated medical procedure, the simulation software utilizes the parameters generated by the one or more sensors to simultaneously track in parallel the performance metrics and provide real-time imaging guidance to the operator via the simulated imaging feed output display.

14. The method of claim 11, wherein the predefined benchmarks are utilized to evaluate the operator's performance with respect to:
  protocol adherence metrics indicating whether tasks associated with performing the simulated medical procedure were correctly completed, and whether the tasks were performed in an appropriate order;

safety metrics indicating whether usage of the one or more medical tools during the simulated medical procedure resulted in errors corresponding to one or more potential health risks;

efficiency metrics indicating whether the simulated medical procedure, or the tasks associated with the simulated medical procedure, is performed in an efficient fashion as defined by the predefined benchmarks; and precision metrics indicating whether the simulated medical procedure, or the tasks associated with the simulated medical procedure, is performed by the operator with a level of precision as defined by the predefined benchmarks.

15. The method of claim 11, wherein the one or more sensors include one or more pressure-measuring sensors and the parameters generated by the pressure-measuring sensors are utilized to evaluate whether excessive pressure was applied as defined by the predefined benchmarks.

16. The method of claim 11, wherein:

the phase data defining the plurality of phases includes a first simulation phase, a second simulation phase, and a third simulation phase;

wherein the phase data further includes:
- one or more conditions defining when the first simulation phase is active;
- one or more conditions defining when the second simulation phase is active; and
- one or more conditions defining when the third simulation phase is active;

the sub-step data for each of the plurality of phases in the simulated medical procedure links or associates each of the sub-steps with one of the plurality of phases;

the one or more data structures defining the simulated medical procedure further includes error condition data for each of the of the plurality of phases, wherein:
- the error condition data defines a third list of conditions for detecting occurrences of errors during the simulated medical procedure and the third list of conditions includes:
  - one or more conditions defining when an error has occurred during the first simulation phase;
  - one or more conditions defining when an error has occurred during the second simulation phase; and
  - one or more conditions defining when an error has occurred during the third simulation phase; and the error condition data for each of the plurality of phases links or associates each of the third list of conditions to at least one of the plurality of phases.

17. The method of claim 16, wherein:

during the operator's performance of the simulated medical procedure, the simulation software is further configured to monitor or track the operator's performance, at least in part, by:
- accessing the phase data stored in the one or more data structures to determine when the first simulation phase, the second simulation phase, and the third simulation phase become active;
- accessing the sub-step data stored in the one or more data structures to determine when each of the plurality of sub-steps become active; and
- accessing the error condition data stored in the one or more data structures to detect error occurrences during the simulated medical procedure.

18. The method of claim 11, wherein:

the simulation software enables a plurality of simulated medical procedures to be performed; and for each of the plurality of simulated medical procedures, the simulation software stores different phase data, different sub-step data, different dependency data, and different benchmark data.

19. The method of claim 11, wherein the one or more data structures include one or more tables.

20. The method of claim 11, wherein the benchmark value is updated based on a plurality of simulation results, wherein each one of the plurality of simulation results is a result of a simulation performed by a medical practitioner.

* * * * *